(12) United States Patent
Beigelman et al.

(10) Patent No.: US 6,395,713 B1
(45) Date of Patent: May 28, 2002

(54) COMPOSITIONS FOR THE DELIVERY OF NEGATIVELY CHARGED MOLECULES

(75) Inventors: Leonid Beigelman, Longmont; Jasenka Matulic-Adamic, Boulder; Alex Karpeisky, Layfayette; Peter Haeberli, Berthoud; David Sweedler, Louisville; Mark Reynolds, Layfayette; Nilabh Chaudhary, Superior; John Min, Longmont, all of CO (US)

(73) Assignee: Ribozyme Pharmaceuticals, Inc., Boulder, CO (US)

( * ) Notice: Subject to any disclaimer, the term of this patent is extended or adjusted under 35 U.S.C. 154(b) by 0 days.

(21) Appl. No.: 09/120,520

(22) Filed: Jul. 21, 1998

Related U.S. Application Data

(60) Provisional application No. 60/053,517, filed on Jul. 23, 1997, and provisional application No. 60/072,967, filed on Jan. 29, 1998.

(51) Int. Cl.[7] .................... A01N 43/04; A61K 31/70; C12N 5/00; C12N 15/00

(52) U.S. Cl. .................... 514/44; 21/2; 424/450; 424/422; 424/423; 424/449; 554/105; 564/159; 564/157; 564/511; 435/240.2; 435/172 B; 435/172.1; 560/158; 560/159; 560/180; 560/190

(58) Field of Search .................... 514/12, 44, 21, 514/560; 530/345, 300; 564/159, 157, 511; 560/158, 189, 190, 159; 536/22.1; 435/240.2, 172.3, 172.1; 424/422, 423, 427, 428, 449, 450; 264/4.1, 4.33, 436; 554/105

(56) References Cited

U.S. PATENT DOCUMENTS

| | | | |
|---|---|---|---|
| 4,897,355 A | 1/1990 | Eppstein et al. | |
| 5,208,036 A | 5/1993 | Epstein et al. | |
| 5,279,833 A | 1/1994 | Rose | |
| 5,283,185 A | 2/1994 | Epand et al. | |
| 5,334,761 A | 8/1994 | Gebeyehu et al. | |
| 5,527,928 A | 6/1996 | Nantz et al. | |
| 5,552,155 A | 9/1996 | Bailey et al. | |
| 5,578,475 A | 11/1996 | Jessee | |
| 5,676,954 A | 10/1997 | Brigham | |
| 5,705,693 A | * | 1/1998 | DePrince et al. |
| 5,777,153 A | * | 7/1998 | Lin et al. |

FOREIGN PATENT DOCUMENTS

| | | |
|---|---|---|
| WO | WO 91/18012 | 11/1991 |

OTHER PUBLICATIONS

Bailey et al., 1997, Biochemistry, 36, p. 1628.*
Felgner, 1993, J. Liposome Res, vol.3, pp 3–16.*
Stewart et al., 1992, Human Gene Therapy, vol.3, pp 267–275.*
Akhtar et al., 1992, Trends Cell Bio., 2, 139.
Bailey et al., 1997, Biochemistry, 36, 1628.
Bangham, 1965, J. Mol. Biol. 13, 238–252.
Bennett et al., 1992 Mol. Pharmacol., 41, 1023–33.
Capaccioli et al., 1993, BBRC, 197,818–25.
Cotten et al., 1990, Proc. Nat. Acad. Sci. USA 87 , 4033.
Felgner et al., 1987, PNAS 84, 7413–7417.
Felgner, 1990, Advanced Drug Delivery Reviews, 5,162–187.
Felgner 1993, J. Liposome Res., 3,3–16.
Ramila et al., 1993 J. Biol. Chem., 268,16087–16090.
Stewart et al., 1992, Human Gene Therapy, 3, 267–275.
Wagner et al., 1991, Proc. Nat. Acad. Sci. USA 88, 4255.
Wagner et al., Proc. Nat. Acad. Sci. USA 87, 3410.
Wu et al., J. Biol. Chem. 266, 14338.
Xu et al., 1996, Biochemistry 35, 5616.
Zenke et al., 1990, Proc. Nat. Acad. Sci. USA 87, 3655.
International Search Report, PCT/US98/15129, mailed Oct. 29, 1998.

\* cited by examiner

*Primary Examiner*—Avis M. Davenport
(74) *Attorney, Agent, or Firm*—McDonnell Boehnen Hulbert & Berghoff

(57) ABSTRACT

This invention features permeability enhancer molecules, and methods, to increase membrane permeability of negatively charged polymers thereby facilitating cellular uptake of such polymers.

13 Claims, 23 Drawing Sheets

Figure 1A: Novel Classes of Cationic Lipids

I. Diamino Carboxylic acid-Based Cationic Lipid

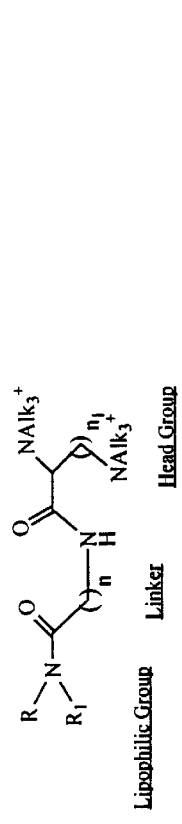

n = 1-3, n₁ = 2-5

R,R₁ = C12-C22 saturated or unsaturated (1-4 double bonds) alkyl chain.
R₂,R₃ = H, acyl, alkyl, carboxamidine, N-alkyl (aryl, acyl, PEG) substituted carboxamidine, PEG, or combination thereof.
Alk = methyl, hydroxyethyl or combination thereof.

II. Quarternary Diamino Carboxylicacid-Based Cationic Lipid

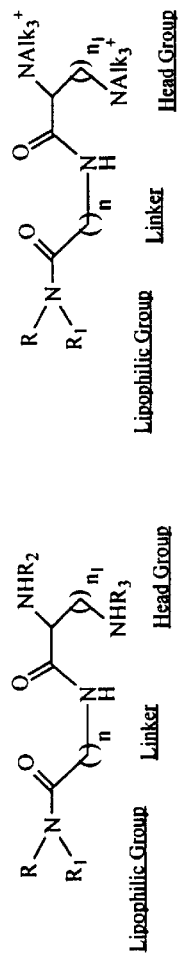

III. Guanidinium-Based Cationic Lipid

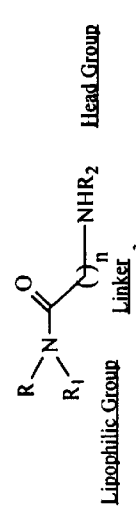

R₂ = H, acyl, alkyl, PEG

IV. Mono Amino-Based Cationic Lipid

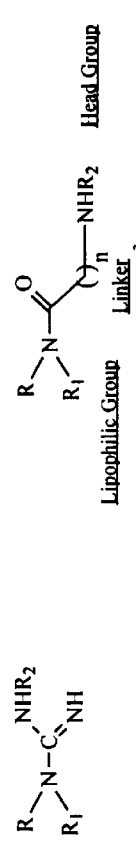

R₂ = H, carboxamidine, N-alkyl (aryl, acyl, PEG) substituted carboxamidine, PEG

V. Polyamine-Based Cationic Lipid

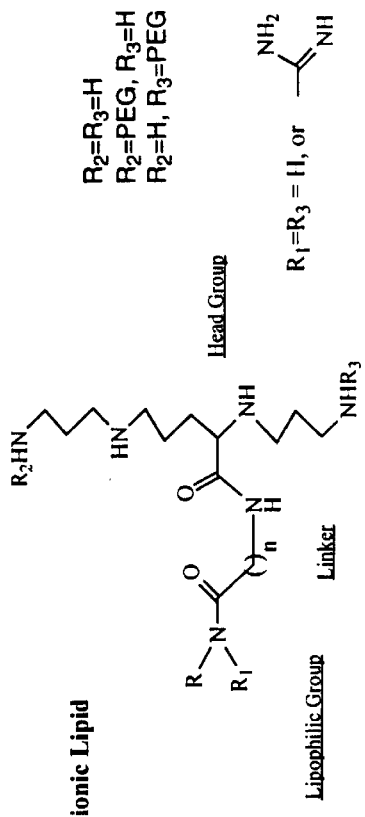

R₂=R₃=H
R₂=PEG, R₃=H
R₂=H, R₃=PEG

R₁=R₃ = H, or

Figure 1B: Mono Amino-Based Cationic Lipid

Class IV

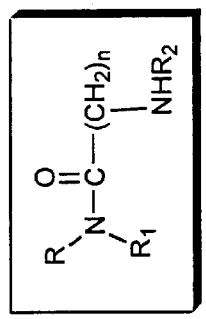

Class V

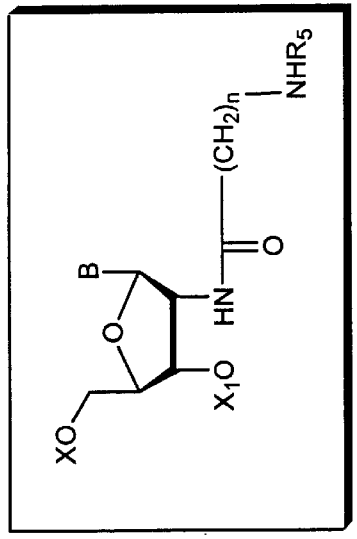

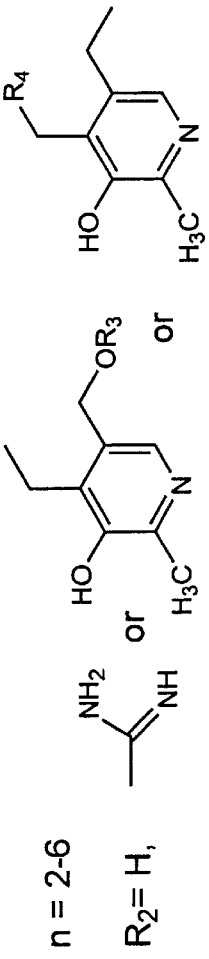

R,R$_1$ = C12-C22 saturated or unsaturated (1-4 double bonds) alkyl chain.

n = 2-6

R$_2$ = H, $\underset{NH_2}{\overset{}{C}}$ or $\underset{NH}{\overset{}{C}}$

R$_3$ = H, PO$_3$H$_2$, PEG
R$_4$ = OH, NH$_2$, =O, O-PEG
R$_5$ = H, carboxamidine
X= X1=R, R1
X=R, X1=R1, X=R1, X1=R
X=PEG, X1=H
X=H, X1=PEG
B= nucleic acid base (modified or unmodified) or H PEG: or PEG 2000 carbonyl, PEG 5000 carbonyl
methoxypolyoxyethylene carbonyl (Ave. Mol. Wt. = 2000 or 5000)
CO-PEG2000 - amide
COOPEG - carbamate

Figure 1C: Glycerol derived cationic lipids
General formula:
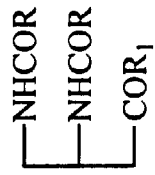
R = saturated or unsaturated (1-4 double bonds) alkyl chains (12-22C)
$R_1$ = TREN, N,N'-di-carboxamidine TREN, lysyl, arginyl, ornithyl, homoarginyl, histidyl, aminopropylimidazole, spermine carboxylic acid.

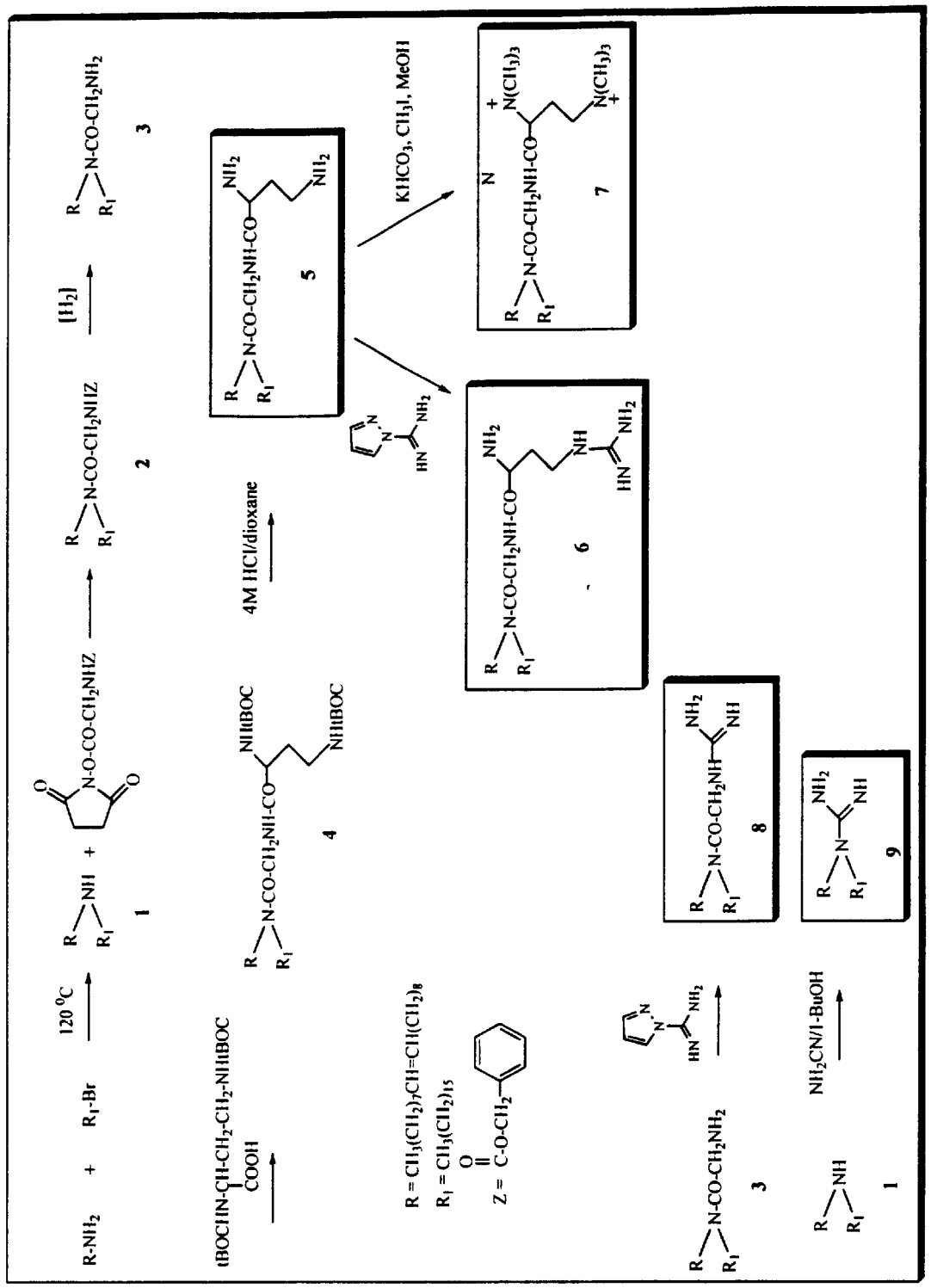
Figure 2: Synthesis of diaminobutyric acid and guanidinium based cationic lipids

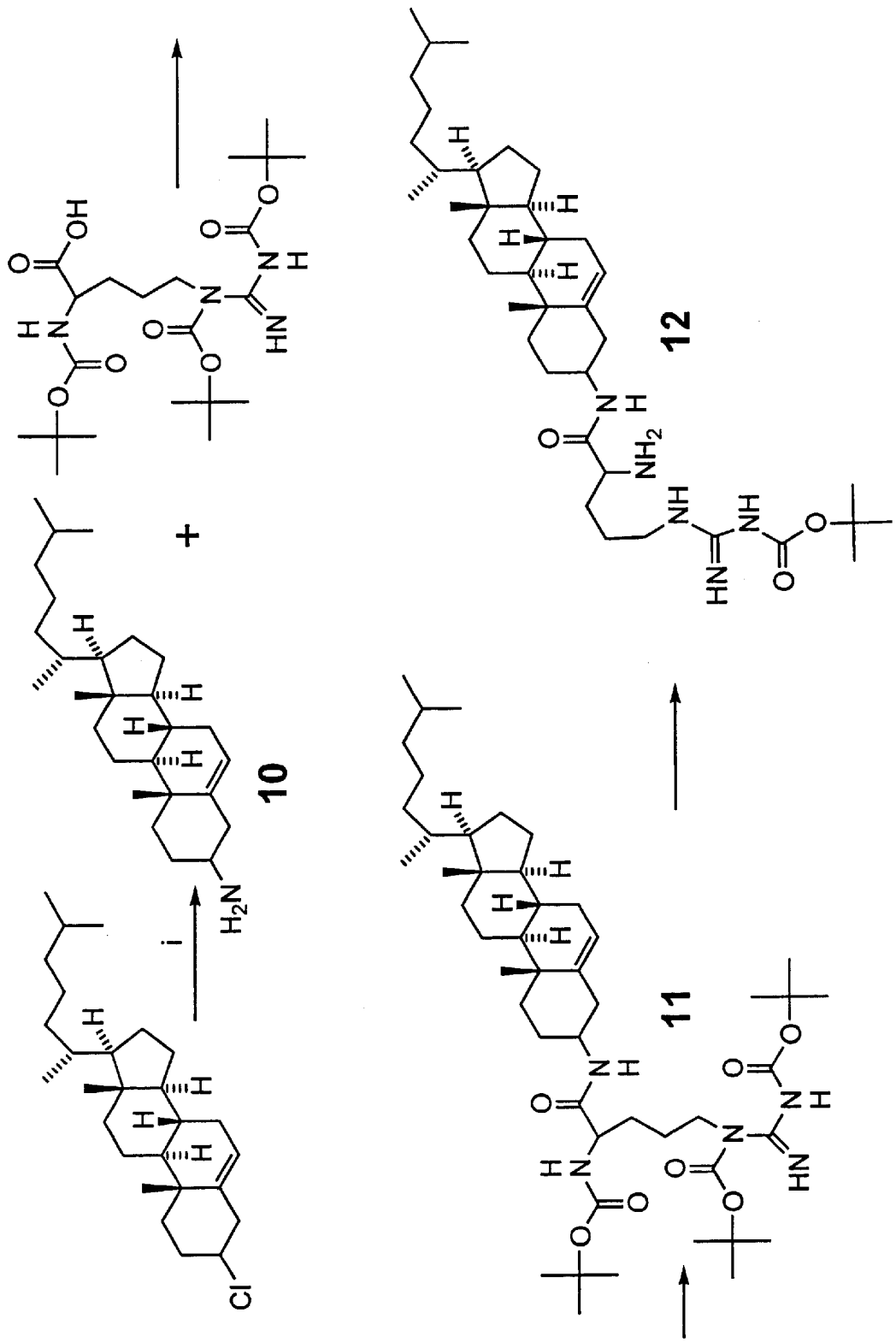
Figure 3: Synthesis of DS 46596 (12)

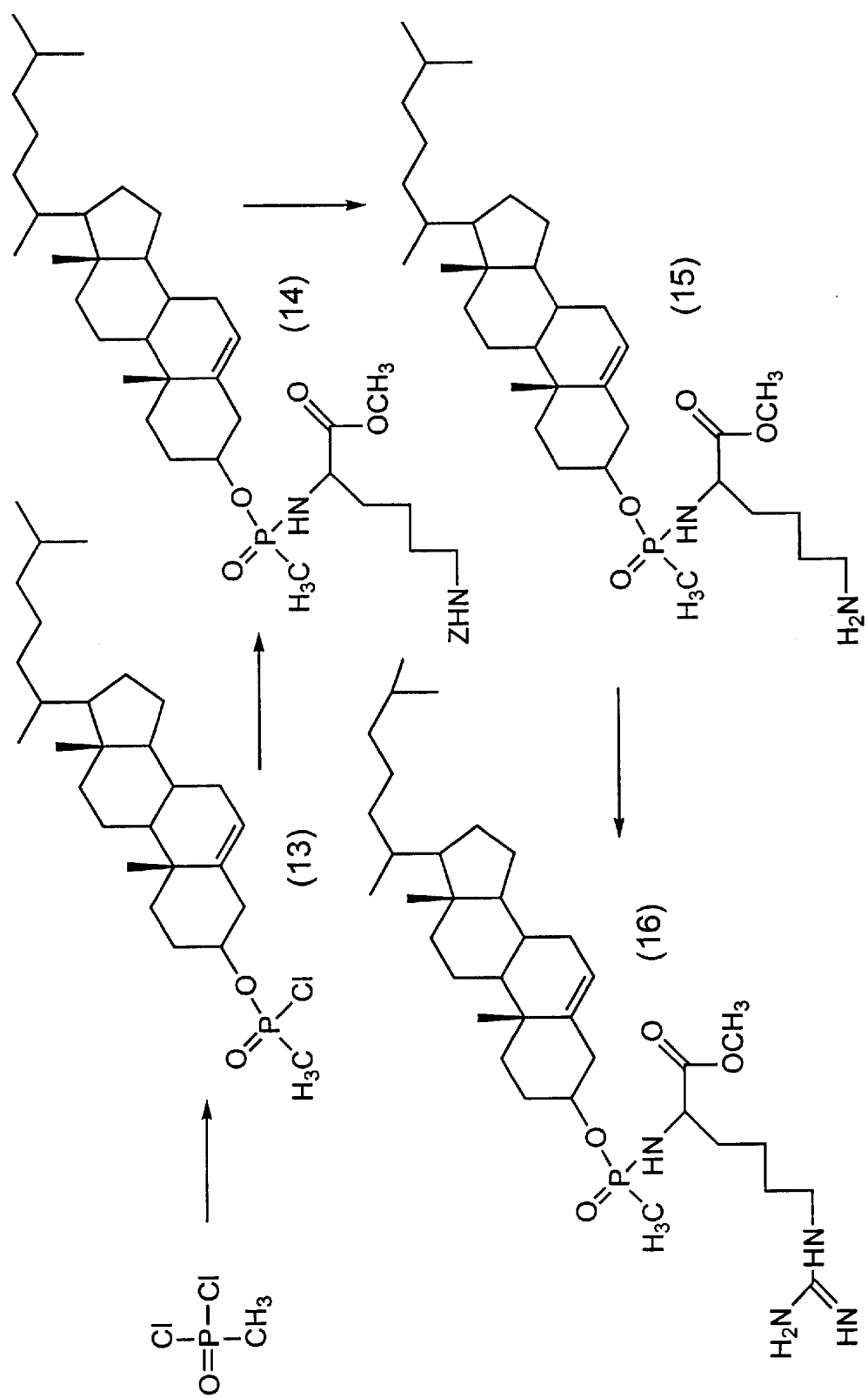
Figure 4: Synthesis of PH 55933 (15), 55938 (16)

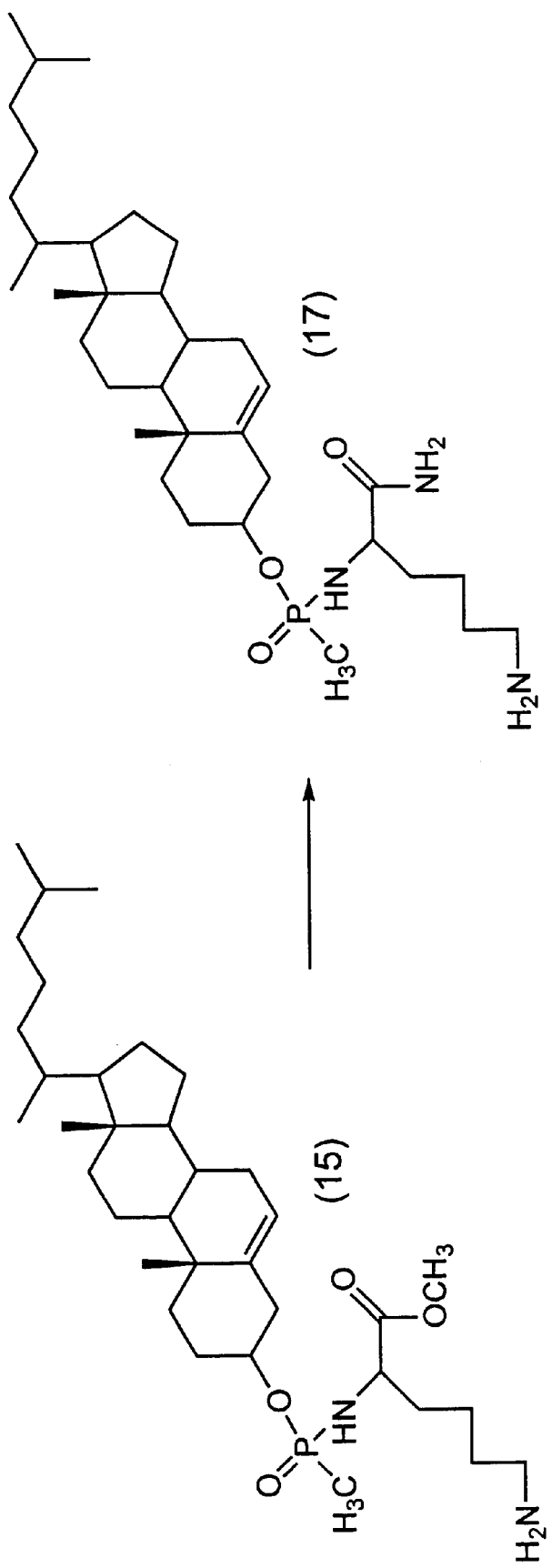
*Figure 5: Synthesis of PH 55939 (17)*

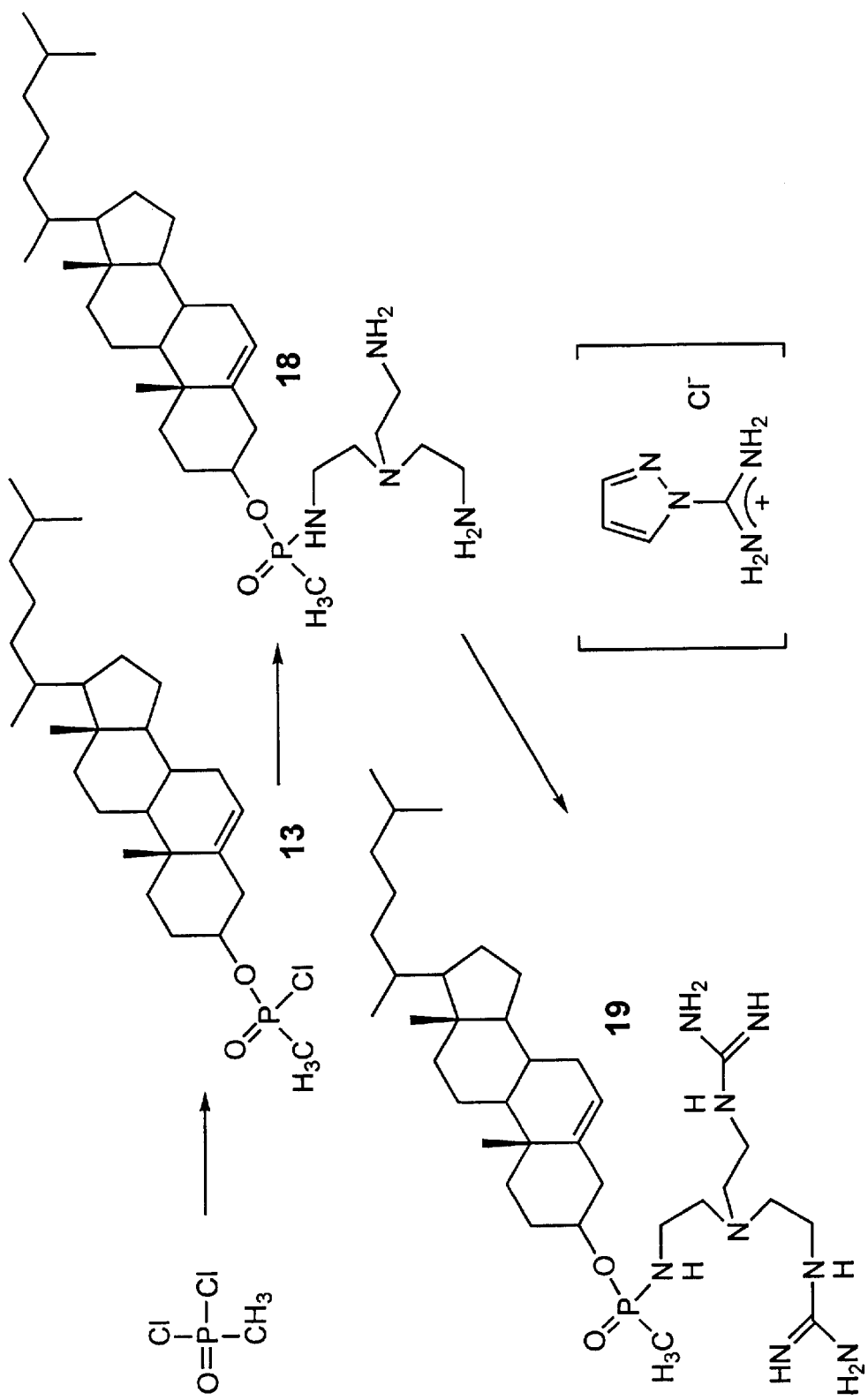
Figure 6: Synthesis of PH 55941 (18), 55942 (19)

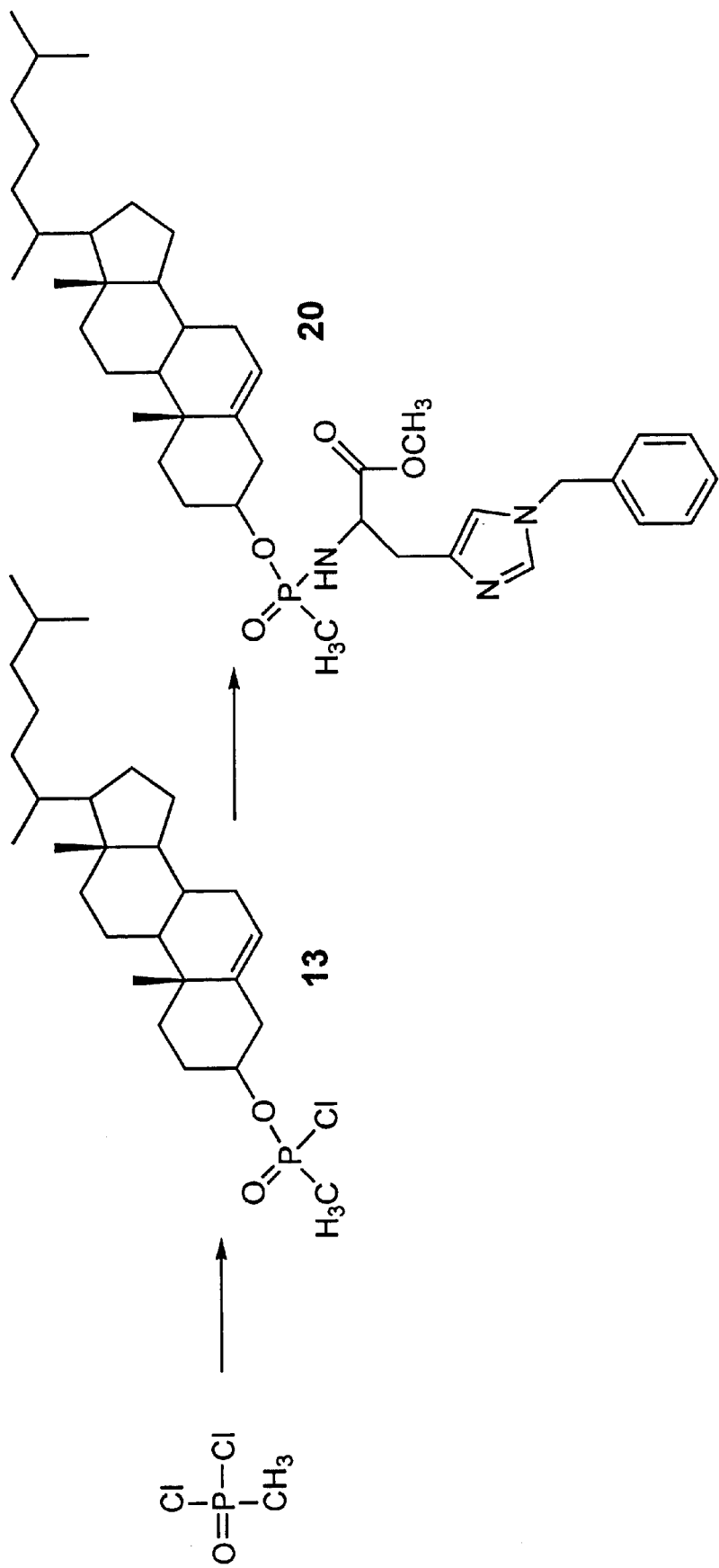
*Figure 7: Synthesis of PH55943 (20)*

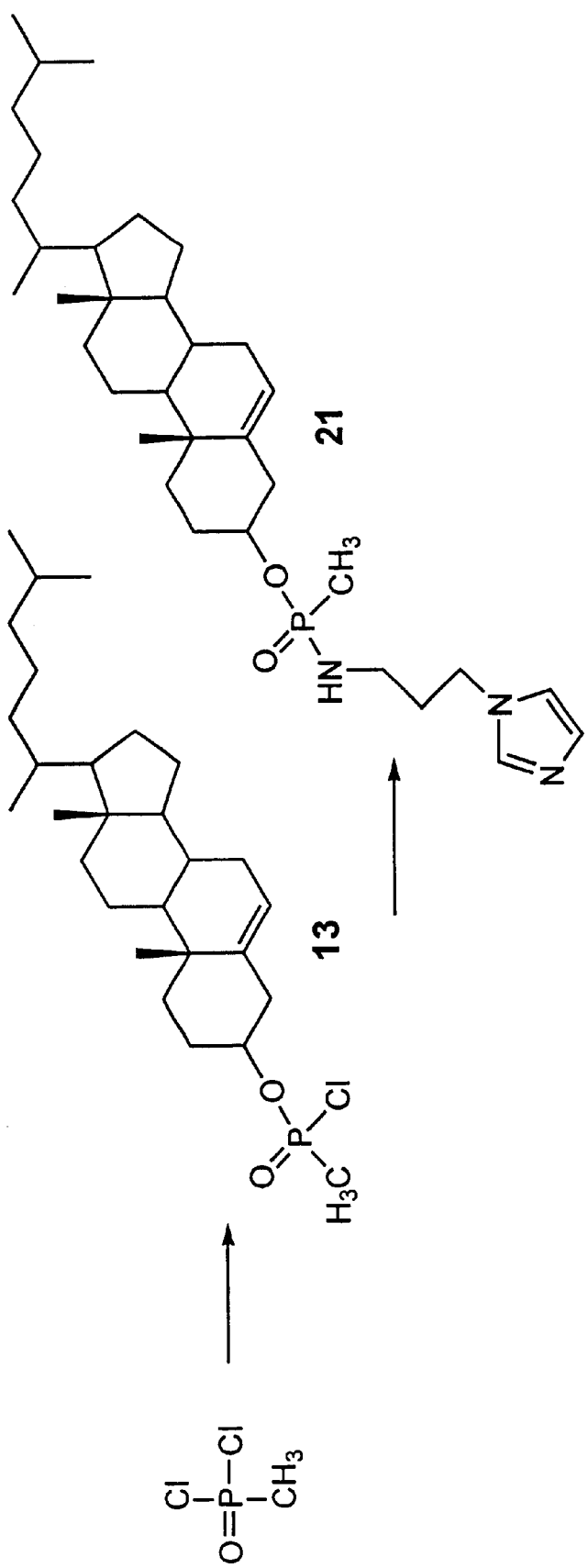
Figure 8: Synthesis of PH 55945 (21)

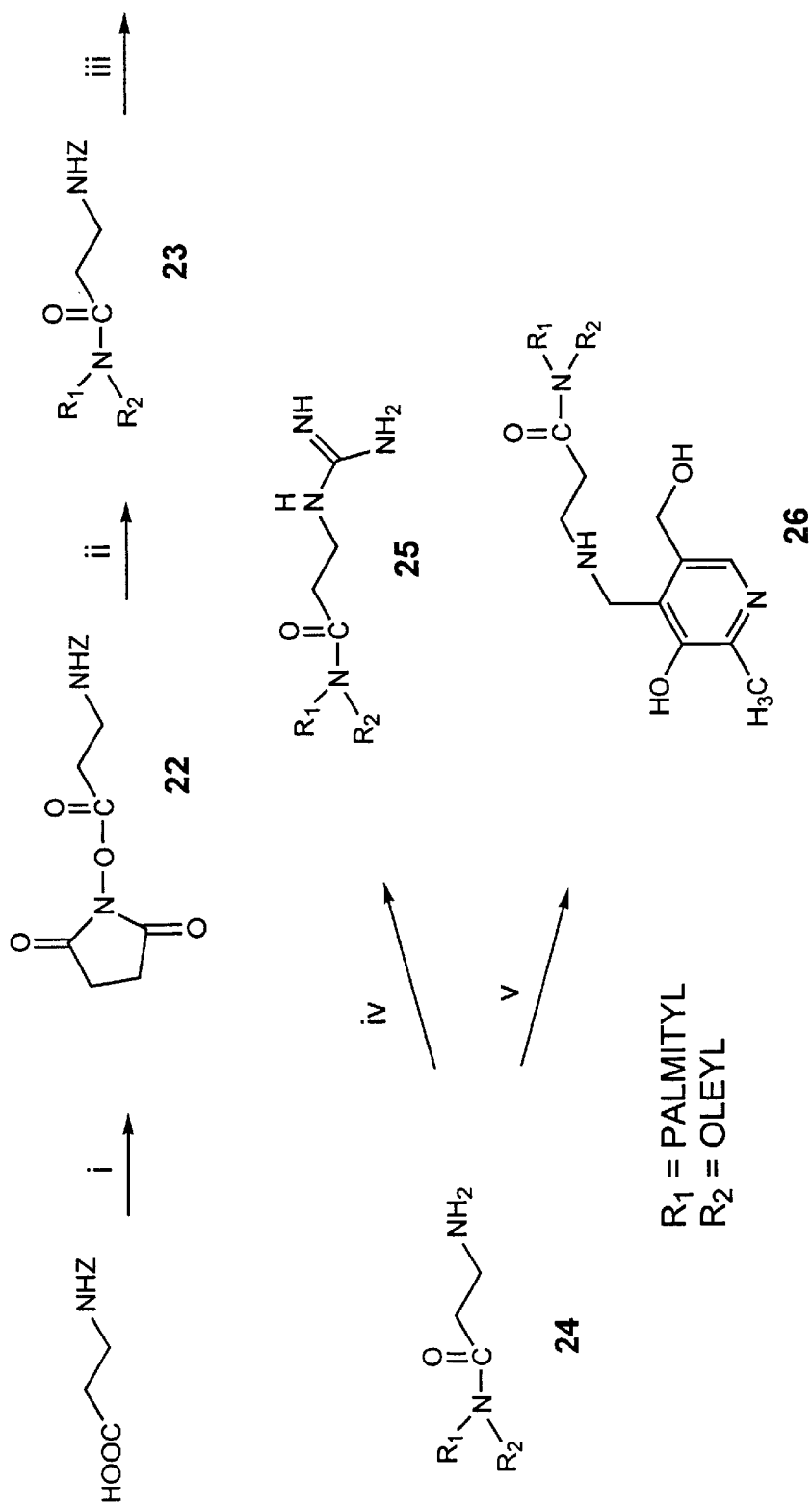
Figure 9: VITAMIN $B_6$ and $\beta$-Ala-BASED CATIONIC LIPIDS
REAGENTS AND CONDITIONS: i) N-hydroxysuccinimide, DCC; ii) $HNR_2$, $Et_3N$; iii) 10% Pd/C, 1,4-cyclohexadiene; iv) a: pyridoxal/EtOH, b: $NaBH_4$; v) 1H-pyrazole-1-carboxamidine/THF-MeOH

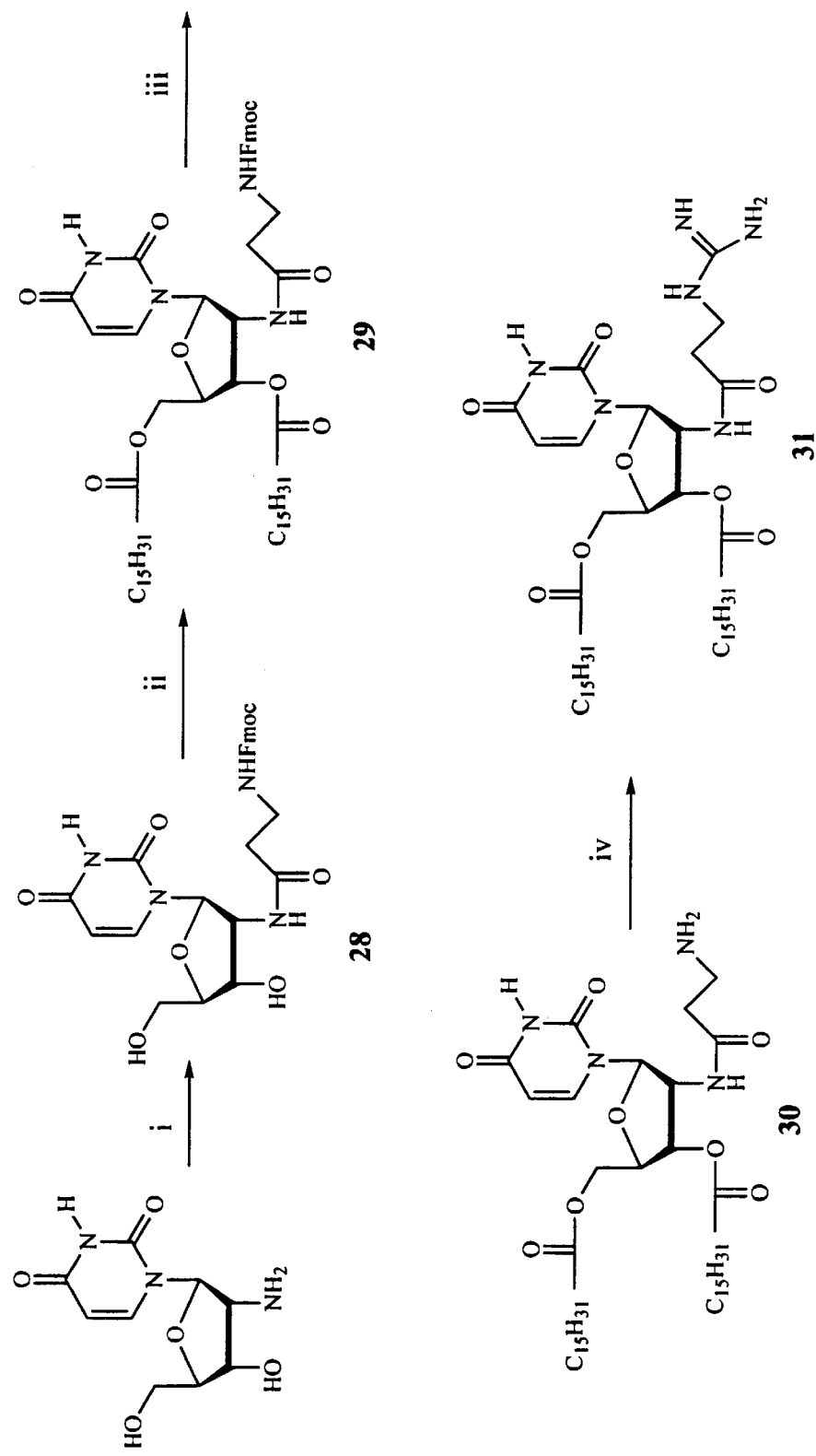
Figure 10: 2'-Aminouridine-Based Cationic Lipids
Reagents and conditions: i) N-Fmoc-b-Ala, EEDQ/MeOH; ii) C₁₅H₃₁COCl/Py; iii) morpholine/CH₂Cl₂; iv) 1H-pyrazole-1-carboxamidine/THF-MeOH

Figure 11: VITAMIN B₆ -CHOLESTEROL CONJUGATE
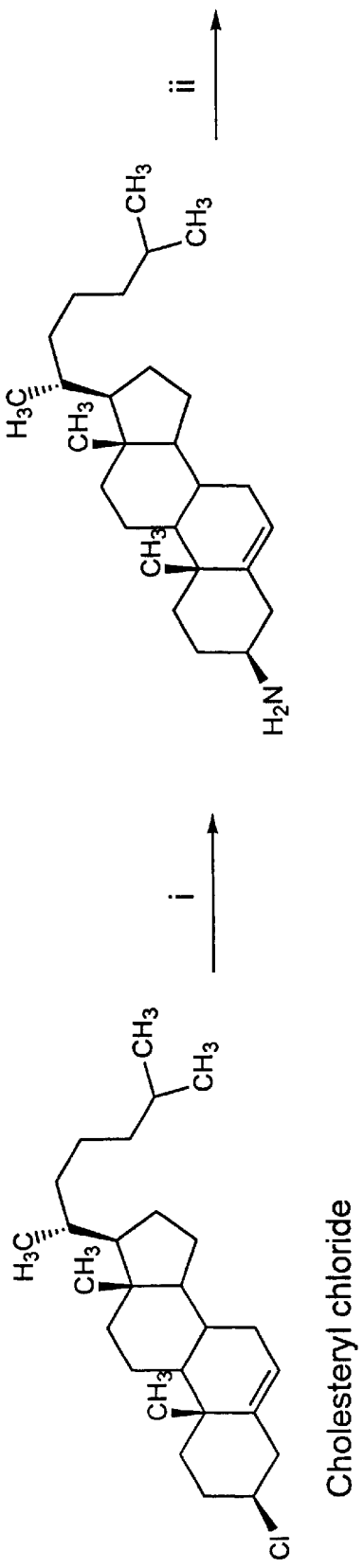
Cholesteryl chloride
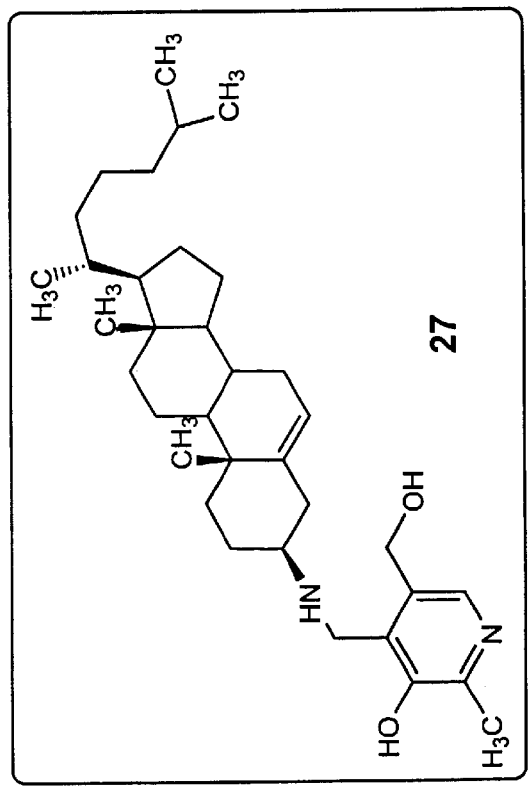
27
REAGENTS AND CONDITIONS: i) NH₃/MEOH; ii) reductive amination of pyridoxal

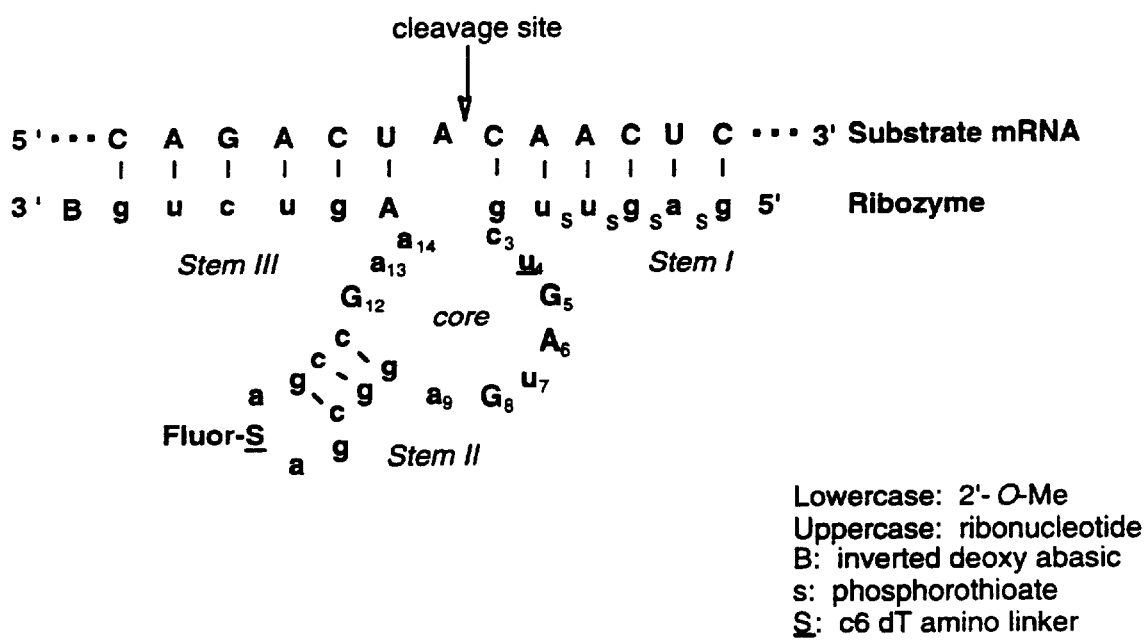
Figure 13. Structure of fluorescein-conjugated ribozyme and its substrate mRNA sequence.

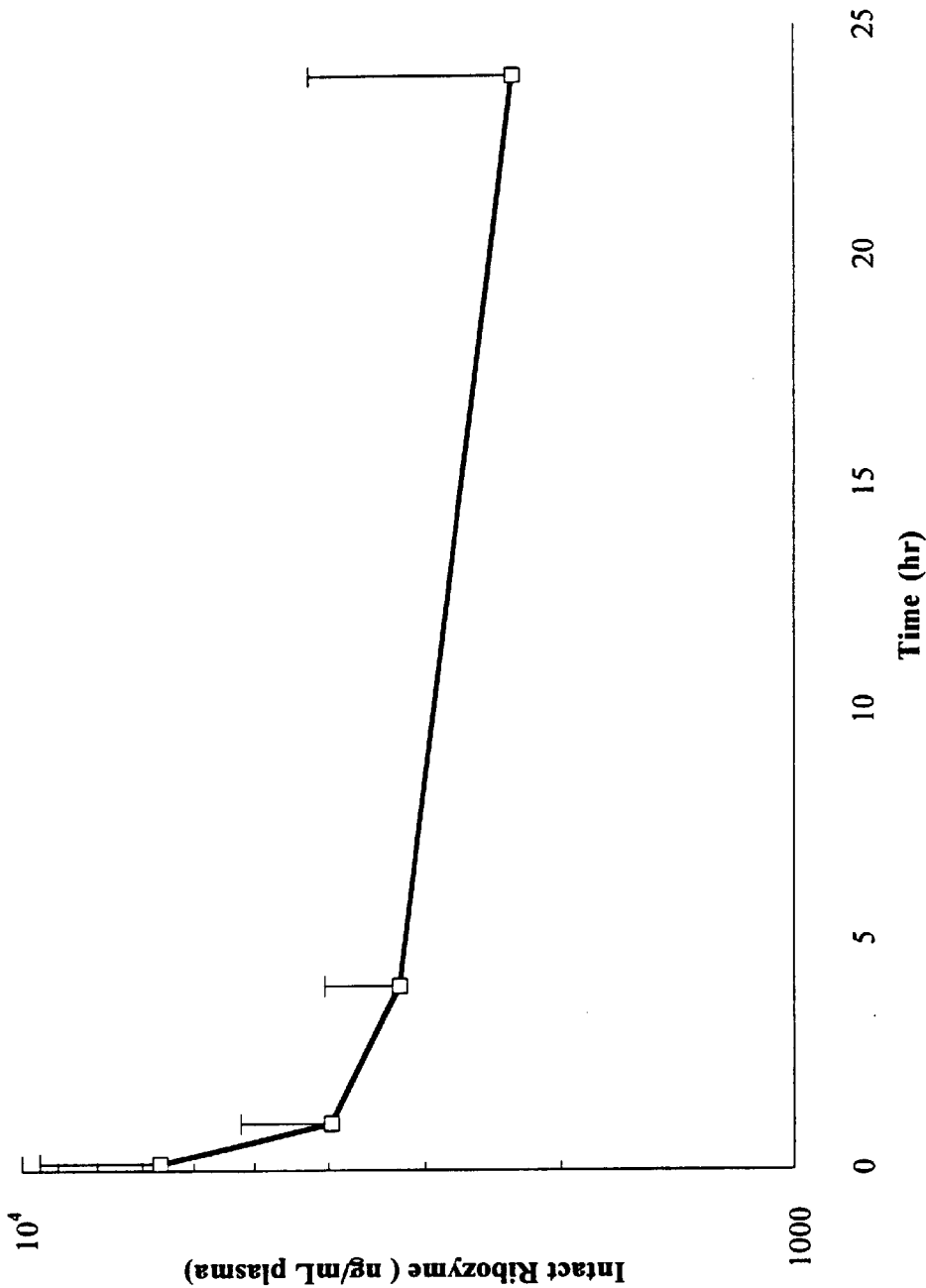
Figure 15: Concentration of Intact Ribozyme after Intravenous Administration of EPC:CHOL:DOTAP:DSPE-PEG$_{2000}$ Liposome Encapsulated Ribozyme

COMPOSITIONS FOR THE DELIVERY OF NEGATIVELY CHARGED MOLECULES

This application is based upon and claims priority from U.S. Provisional application Ser. No. 60/053,517 filed Jul. 23, 1997 and Ser. No. 60/072,967 filed Jan. 29, 1998.

BACKGROUND OF THE INVENTION

The following is a brief description of the delivery of biopolymers. This summary is not meant to be complete but is provided only for understanding of the invention that follows. This summary is not an admission that all of the work described below is prior art to the claimed invention.

Trafficking of large, charged molecules into living cells is highly restricted by the complex membrane systems of the cell. Specific tranporters allow the selective entry of nutrients or regulatory molecules, while excluding most exogenous molecules such as nucleic acids and proteins. The two major strategies for improving the transport of foreign nucleic acids into cells are the use of viral vectors or cationic lipids and related cytofectins. Viral vectors can be used to transfer genes efficiently into some cell types, but they cannot be used to introduce chemically synthesized molecules into cells. An alternative approach is to use delivery formulations incorporating cationic lipids, which interact with nucleic acids through one end and lipids or membrane systems through another (for a review see Felgner, 1990, *Advanced Drug Delivery Reviews*, 5,162–187; Felgner 1993, *J. Liposome Res.*, 3,3–16). Synthetic nucleic acids as well as plasmids may be delivered using the cytofectins, although their utility is often limited by cell-type specificity, requirement for low serum during transfection, and toxicity.

Since the first description of liposomes in 1965, by Bangham (*J. Mol. Biol.* 13, 238–252), there has been a sustained interest and effort in the area of developing lipid-based carrier systems for the delivery of pharmaceutically active compounds. Liposomes are attractive drug carriers since they protect biological molecules from degradation while improving their cellular uptake.

One of the most commonly used classes of liposomes formulation for delivering polyanions (e.g., DNA) are those that contain cationic lipids. Lipid aggregates can be formed with macromolecules using cationic lipids alone or including other lipids and amphiphiles such as phosphatidylethanolamine. It is well known in the art that both the composition of the lipid formulation as well as its method of preparation have effect on the structure and size of the resultant anionic macromolecule-cationic lipid aggregate. These factors can be modulated to optimize delivery of polyanions to specific cell types in vitro and in vivo. The use of cationic lipids for cellular delivery of biopolymers have several advantages. The encapsulation of anionic compounds using cationic lipids is essentially quantitative due to electrostatic interaction. In addition, it is believed that the cationic lipids interact with the negatively charged cell membranes initiating cellular membrane transport (Akhtar et al., 1992, *Trends Cell Bio.*, 2, 139; Xu et al., 1996, *Biochemistry* 35, 5616).

The transmembrane movement of negatively charged molecules such as nucleic acids may therefore be markedly improved by coadministration with cationic lipids or other permeability enhancers (Bennett et al., 1992 *Mol. Pharmacol.*, 41, 1023–33; Capaccioli et al., 1993, *BBRC*, 197,818–25; Ramila et al., 1993 *J. Biol. Chem.*, 268, 16087–16090; Stewart et al., 1992, *Human Gene Therapy*, 3, 267–275). Since the introduction of the cationic lipid DOTMA and its liposomal formulation Lipofectin™ (Felgner et al., 1987, *PNAS* 84, 7413–7417; Eppstein et al., U.S. Pat. No. 4,897,355), a number of other lipid-based delivery agents have been described primarily for transfecting mammalian cells with plasmids or antisense molecules (Rose, U.S. Pat. No. 5,279,833; Eppand et al. U.S. Pat. No. 5,283,185; Gebeyehu et al., U.S. Pat. No. 5,334,761; Nantz et al., U.S. Pat. No. 5,527,928; Bailey et al., U.S. Pat. No. 5,552,155; Jesse, U.S. Pat. No. 5,578,475). However, each formulation is of limited utility because it can deliver plasmids into some but not all cell types, usually in the absence of serum (Bailey et al., 1997, *Biochemistry*, 36, 1628). Concentrations (charge and/or mass ratios) that are suitable for plasmid delivery (~5,000 to 10,000 bases in size) are generally not effective for oligonucleotides such as synthetic ribozymes or antisense molecules (~10 to 50 bases). Also, recent studies indicate that optimal delivery conditions for antisense oligonucleotides and ribozymes are different, even in the same cell type. However, the number of available delivery vehicles that may be utilized in the screening procedure is highly limited, and there continues to be a need to develop transporters that can enhance nucleic acid entry into many types of cells.

Epstein et al., U.S. Pat. No. 5,208,036, disclose a liposome, LIPOFECTIN™, that contains an amphipathic molecule having a positively charged choline head group (water soluble) attached to a diacyl glycerol group (water insoluble). Promega (Wisconsin) markets another cationic lipid, TRANSFECTAM™, which can help introduce nucleic acid into a cell.

Wagner et al., 1991, *Proc. Nat. Acad. Sci. USA* 88, 4255; Cotten et al., 1990, *Proc. Nat. Acad. Sci. USA* 87, 4033; Zenke et al., 1990, *Proc. Nat. Acad. Sci. USA* 87, 3655; and Wagner et al., *Proc. Nat. Acad. Sci. USA* 87, 3410, describe transferrin-polycation conjugates which may enhance uptake of DNA into cells. They also describe the feature of a receptor-mediated endocytosis of transferrin-polycation conjugates to introduce DNA into hematopoietic cells.

Wu et al., *J. Biol. Chem.* 266, 14338, describe in vivo receptor-mediated gene delivery in which an asialoglycoprotein-polycation conjugate consisting of asialoorosomucoid is coupled to poly-L-lysine. A soluble DNA complex was formed capable of specifically targeting hepatocytes via asialoglycoprotein receptors present on the cells.

Biospan Corporation International PCT Publication No. WO 91/18012, describe cell internalizable covalently bonded conjugates having an "intracellularly cleavable linkage" such as a "disulfide cleavable linkage" or an enzyme labile ester linkage.

Brigham, U.S. Pat. No. 5,676,954 describes a method for the expression of nucleic acid following transfection into a target organ consisting of mammalian cells.

The references cited above are distinct from the presently claimed invention since they do not disclose and/or contemplate the delivery vehicles of the instant invention.

SUMMARY OF THE INVENTION

This invention features cationic lipid-based compositions to facilitate delivery of negatively charged molecules into a biological system such as animal cells. The present invention discloses the design, synthesis, and cellular testing of novel agents for the delivery of negatively charged molecules in vitro and in vivo. Also disclosed are screening procedures for identifying the optimal delivery vehicles for any given nucleic acid and cell type. In general, the transporters described here were designed to be used either individually or as part of a multicomponent system. The compounds of the invention generally shown in FIG. 1, are expected to improve delivery of negatively charged molecules into a number of cell types originating from different tissues, in the presence or absence of serum.

The "negatively charged molecules" are meant to include molecules such as nucleic acid molecules (e.g., RNA, DNA, oligonucleotides, mixed polymers, peptide nucleic acid, and the like), peptides (e.g., polyaminoacids, polypeptides, proteins and the like), nucleotides, pharmaceutical and biological compositions, that have negatively charged groups that can ion-pair with the positively charged head group of the cationic lipids of the invention In a first aspect the invention features a cationic lipid having the formula I:

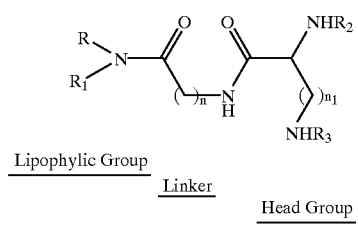

Lipophylic Group
Linker
Head Group wherein, n is 1, 2 or 3 carbon atoms; $n_1$ is 2, 3, 4 or 5 carbon atoms; R and $R_1$ independently represent C12–C22 alkyl chain which are saturated or unsaturated, wherein the unsaturation is represented by 1–4 double bonds; and $R_2$ and $R_3$ are independently H, acyl, alkyl, carboxamidine, aryl, acyl, substituted carboxamidine, polyethylene glycol (PEG) or a combination thereof.

In a second aspect the invention features a cationic lipid having the formula II:

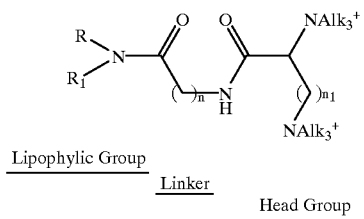

Lipophylic Group
Linker
Head Group wherein, n is 1, 2 or 3 carbon atoms; $n_1$ is 2, 3, 4 or 5 carbon atoms; R and R independently represent C12–C22 alkyl chain which are saturated or unsaturated, wherein the unsaturation is represented by 1–4 double bonds; and Alk represents methyl, hydroxyalkyl (e.g., hydroxymethyl and hydroxyalkyl) or a combination thereof.

In a third aspect the invention features a cationic lipid having the formula III:

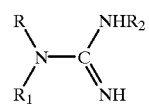

wherein, R and $R_1$ independently represent C12–C22 alkyl chain which are saturated or unsaturated, wherein the unsaturation is represented by 1–4 double bonds; and $R_2$ is H, PEG, acyl or alkyl.

In a fourth aspect the invention features a cationic lipid having the formula IV:

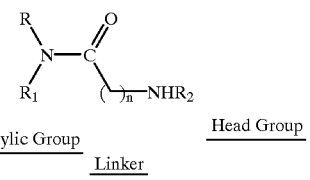

Lipophylic Group    Linker    Head Group wherein, n is 1–6 carbon atoms; R and $R_1$ independently represent C12–C22 alkyl chain which are saturated or unsaturated, wherein the unsaturation is represented by 1–4 double bonds; and $R_2$ is H, carboxamidine, alkyl, acyl, aryl, PEG, substituted carboxamidine

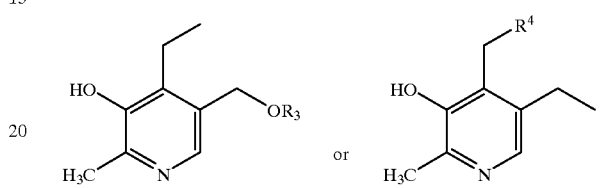

where $R_3$ is H, or $PO_3H_2$ and $R_4$ is OH, $NH_2$ or $=O$.

In a fifth aspect the invention features a cationic lipid having the formula V:

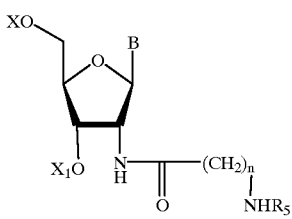

wherein, n is 1–6 carbon atoms; X and $X_1$ independently represent C12–C22 alkyl chain which are saturated or unsaturated wherein the unsaturation is represented by 1–4 double bonds, B is a nucleic acid base or H; and $R_5$ is H, PEG, or carboxamidine.

In a sixth aspect the invention features a cationic lipid having the formula VI:

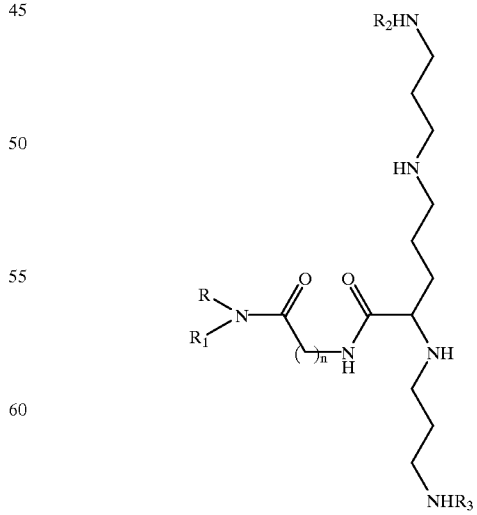

wherein, n is 1, 2 or 3 carbon atoms; R and $R_1$ independently represent C12–C22 alkyl chain which are saturated or unsaturated, wherein the unsaturation is represented by 1–4 double bonds; and $R_2$ and is independently H, polyethylene glycol (PEG) or

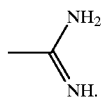

For the above-referenced formulae, N, O, and H are Nitrogen, Oxygen and Hydrogen, according to the abbreviations well-known in the art.

In a seventh aspect the invention features a cationic lipid having the formula VII:

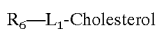

wherein, $R_6$ is selected from the group consisting of arginyl methyl ester, arginyl amide, homoarginyl methyl ester, homoarginyl amide, ornithine methyl ester, ornithine amide, lysyl methyl ester, lysyl amide, triethylenetetramine (TREN), N,N'-di-carboxamidine TREN, N-benzyl histidyl methyl ester, pyridoxyl and aminopropylimidazole. $L_1$ is a linker represented by $R_7PO2$, wherein $R_7$ is H, $CH_3$, or $CH_2CH_3$. Examples of this group of compounds are: PH55933, PH55938, PH55939, PH55941, PH55942, PH55943 and PH55945.

In an eighth aspect the invention features a cationic lipid having the formula VIII:

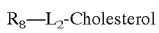

wherein, $R_8$ is selected from the group consisting of arginyl, N-Boc arginyl, homoarginyl, N-Boc homoarginyl ornithine, N-Boc ornithine, N-benzyl histidyl, lysyl, N-Boc lysyl, N-methyl arginyl, N-methyl guanidine, guanidine and pyridoxyl. Is is a linker represented by NH, glycine, N-butyldiamine or guanidine. Examples of this compound is Boc arginine cholesterol amide (DS46596), N-guanyl-cholesterylamide (DS57511).

In a ninth aspect the invention features a cationic lipid having the formula IX:

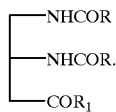

Wherein R is independently a C12–C22 alkyl chain which are saturated or unsaturated, wherein the unsaturation is represented by 1–4 double bonds and $R_1$ is represented by TREN, N,N'-di-carboxamidine TREN, lysyl, arginyl, ornithyl, homoarginyl, histidyl, aminopropylimidazole, spermine carboxylic acid.

By "Head Group" is meant an amino-containing moiety that is positively charged and is capable of forming ion pairs with negatively charged regions of biopolymers such as nucleic acid molecules.

By "lipophilic group" is meant a hydrophobic lipid-containing group that facilitates transmembrane transport of the cationic lipid.

By "linker" is meant a 1–6 atom carbon chain that links the head group with the lipophylic group.

By "ion pair" is meant non-covalent interaction between oppositely charged groups.

Specifically, an "alkyl" group refers to a saturated aliphatic hydrocarbon, including straight-chain, branched-chain, and cyclic alkyl groups. Preferably, the alkyl group has 1 to 12 carbons. More preferably it is a lower alkyl of from 1 to 7 carbons, more preferably 1 to 4 carbons. The alkyl group may be substituted or unsubstituted. When substituted the substituted group(s) is preferably, hydroxy, cyano, alkoxy, $NO_2$ or $N(CH_3)_2$, amino, or SH.

By "alkoxy" is meant an OR group, wherein R is an alkyl.

An "aryl" group refers to an aromatic group which has at least one ring having a conjugated π electron system and includes carbocyclic aryl, heterocyclic aryl and biaryl groups, all of which may be optionally substituted. The preferred substituent(s) on aryl groups are halogen, trihalomethyl, hydroxyl, SH, cyano, alkoxy, alkyl, alkenyl, alkynyl, and amino groups.

The term "alkenyl" group refers to unsaturated hydrocarbon groups containing at least one carbon-carbon double bond, including straight-chain, branched-chain, and cyclic groups. Preferably, the alkenyl group has 1 to 12 carbons. More preferably it is a lower alkenyl of from 1 to 7 carbons, more preferably 1 to 4 carbons. The alkenyl group may be substituted or unsubstituted. When substituted the substituted group(s) is preferably, hydroxyl, cyano, alkoxy, $NO_2$, halogen, $N(CH_3)_2$, amino, or SH.

The term "alkynyl" refers to an unsaturated hydrocarbon group containing at least one carbon-carbon triple bond, including straight-chain, branched-chain, and cyclic groups. Preferably, the alkynyl group has 1 to 12 carbons. More preferably it is a lower alkynyl of from 1 to 7 carbons, more preferably 1 to 4 carbons. The alkynyl group may be substituted or unsubstituted. When substituted the substituted group(s) is preferably, hydroxyl, cyano, alkoxy, =O, =S, $NO_2$ or $N(CH_3)_2$, amino or SH.

An "alkylaryl" group refers to an alkyl group (as described above) covalently joined to an aryl group (as described above).

"Carbocyclic aryl" groups are groups wherein the ring atoms on the aromatic ring are all carbon atoms. The carbon atoms are optionally substituted.

"Heterocyclic aryl" groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, pyrrolo, pyrimidyl, pyrazinyl, imidazolyl and the like, all optionally substituted.

By "acyl" is meant —C(O)R groups, wherein R is an alkyl or aryl.

In a preferred embodiment, the invention features process for the synthesis of the compounds of formula I–IX.

In another preferred embodiment a series of multidomain cellular transport vehicles (MCTV) including one or more lipids of formula I–IX that enhance the cellular uptake and transmembrane permeability of negatively charged molecules in a variety of cell types are described. The lipids of the invention are used either alone or in combination with other compounds with a neutral or a negative charge including but not limited to neutral lipid and/or targeting components, to improve the effectiveness of the lipid formulation in delivering and targeting the negatively charged polymers to cells. Another object is to describe the utility of these delivery vehicles for increasing the transport of other impermeable and/or lipophilic compounds into cells.

By "compounds with neutral charge" is meant compositions which are neutral or uncharged at neutral or physiological pH. Examples of such compounds are cholesterol (i.e., a steroidal alcohol, as defined in Lehninger, *Biochemistry,* 1982 ed., Worth Pub., p. 315) and other steroids, cholesteryl hemisuccinate (CHEMS), dioleoyl phosphatidyl choline, distearoylphosphotidyl choline (DSPC), fatty acids such as oleic acid, phosphatidic acid and its derivatives, phosphatidyl serine, polyethylene glycol-conjugated phosphatidylamine, phosphatidylcholine, phosphatidylethanolamine and related variants, prenylated compounds including farnesol, polyprenols, tocopherol, and their modified forms, diacylsuccinyl glycerols, fusogenic or pore forming peptides, dioleoylphosphotidylethanolamine (DOPE), ceramide and the like.

Targeting components include ligands for cell surface receptors including, peptides and proteins, glycolipids, lipids, carbohydrates, and their synthetic variants.

In yet another preferred embodiment, the cationic lipid molecules of the invention are provided as a lipid aggregate, such as a liposome, and co-encapsulated with the negatively charged polymer to be delivered. Liposomes, which may be unilamellar or multilamellar, can introduce encapsulated material into a cell by different mechanisms. See, Ostro, *Scientific American* 102, January 1987. For example, the liposome can directly introduce its encapsulated material into the cell cytoplasm by fusing with the cell membrane. Alternatively, the liposome can be compartmentalized into an acidic vacuole (i.e., an endosome) having a pH below 7.0. This low pH allows ion-pairing of the encapsulated enhancers and the negatively charged polymer, which facilitates diffusion of the enhancer:polymer complex out of the liposome, the acidic vacuole, and into the cellular cytoplasm.

By "lipid aggregate" is meant a lipid-containing composition (i.e., a composition comprising a lipid according to the invention) wherein the lipid is in the form of a liposome, micelle (non-lamellar phase) or other aggregates with one or more lipids.

In yet another preferred embodiment the invention features a lipid aggregate formulation including phosphatidylcholine (of varying chain length; e.g., egg yolk phosphatidylcholine), cholesterol, a cationic lipid, and 1,2-distearoyl-sn-glycero-3-phosphoethanolamine-polythyleneglycol-2000 (DSPE-PEG$_{2000}$). The cationic lipid component of this lipid aggregate can be any cationic lipid known in the art such as dioleoyl 1,2,-diacyl-3-trimethylammonium-propane (DOTAP). In a preferred embodiment this cationic lipid aggregate comprises a cationic lipid described in any of the Formula I–IX.

In yet another preferred embodiment, polyethylene glycol (PEG) is covalently attached to the cationic lipids of the present invention. The attached PEG can be any molecular weight but is preferably between 2000–5000 daltons.

The molecules and methods of the present invention are particularly advantageous for introducing nucleic acid molecules into a cell. For example, the invention can be used for ribozyme delivery where its target site of action exists intracellularly.

Other features and advantages of the invention will be apparent from the following description of the preferred embodiments thereof, and from the claims.

DESCRIPTION OF THE PREFERRED EMBODIMENTS

The drawings will be first described briefly.
Drawings

FIG. 1 depicts the different classes of cationic lipids of the instant invention.

FIG. 2 depicts a scheme for the synthesis of diaminobutyric and guanidinium-based cationic lipids.

FIG. 3 depicts a scheme for the synthesis of Boc Arginine cholesteryl amide (12; DS46596).

FIG. 4 depicts a scheme for the synthesis of cholesterol-lysine-methyl ester-methylphosphonoamidate (PH55933; 15) and cholesterol-homoarginine-methyl ester methylphosphonoamidate (PH55938; 16).

FIG. 5 depicts a scheme for the synthesis of cholesterol-lysine-amide-methylphosphonoamidate (PH55939; 17).

FIG. 6 depicts a scheme for the synthesis of cholesterol-TREN-methylphosphonoamidate (PH55941; 18) and cholesterol-TREN-bis-guanidinium methylphosphonoamidate (PH55942; 19).

FIG. 7 depicts a scheme for the synthesis of cholesterol-histidine-methylphosphonoamidate (PH55943; 20).

FIG. 8 depicts a scheme for the synthesis of cholesterol-aminopropylimidazole-methylphosphonoamidate (PH55945; 21).

FIG. 9 depicts a scheme for the synthesis of vitamin-B6 and beta-alanine-based cationic lipids.

FIG. 10 depicts a scheme for the synthesis of 2'-aminouridine-based cationic lipids.

FIG. 11 depicts a scheme for the synthesis of vitamin-B6-cholesterol conjugate.

FIG. 12 shows the secondary structure model for seven different classes of enzymatic nucleic acid molecules. Arrow indicates the site of cleavage. --------- indicate the target sequence. Lines interspersed with dots are meant to indicate tertiary interactions.—is meant to indicate base-paired interaction. Group I Intron: P1–P9.0 represent various stem-loop structures (Cech et al., 1994, *Nature Struc. Bio.*, 1, 273). RNase P (M1RNA): EGS represents external guide sequence (Forster et al., 1990, *Science*, 249, 783; Pace et al., 1990, *J. Biol. Chem.*, 265, 3587). Group II Intron: 5'SS means 5' splice site; 3'SS means 3'-splice site; IBS means intron binding site; EBS means exon binding site (Pyle et al., 1994, *Biochemistry*, 33, 2716). VS RNA: I–VI are meant to indicate six stem-loop structures; shaded regions are meant to indicate tertiary interaction (Collins, International PCT Publication No. WO 96/19577). HDV Ribozyme: : I–IV are meant to indicate four stem-loop structures (Been et al., U.S. Pat. No. 5,625,047). Hammerhead Ribozyme: : I–III are meant to indicate three stem-loop structures; stems I–III can be of any length and may be symmetrical or asynmmetrical (Usman et al., 1996, *Curr. Op. Struct. Bio.*, 1, 527). Hairpin Ribozyme: H1–H4 are meant to indicate helices 1–4; Helix 1 and 4 can be of any length; Helix 2 is between 3 and 8 base-pairs long; Y is a pyrimidine; B is guanosine, cytidine or uridine; V is adenosine, guanosine, or cytidine (Burke et al., 1996, *Nucleic Acids & Mol. Biol.*, 10, 129; Chowrira et al., U.S. Pat. No. 5,631,359).

FIG. 13 depicts the structure of fluorescein-conjugated ribozyme and its substrate mRNA sequence. The fluorescein moiety (Fluor), attached through an amino linker, does not reduce the enzymatic activity of the ribozyme.

Figure 12A:
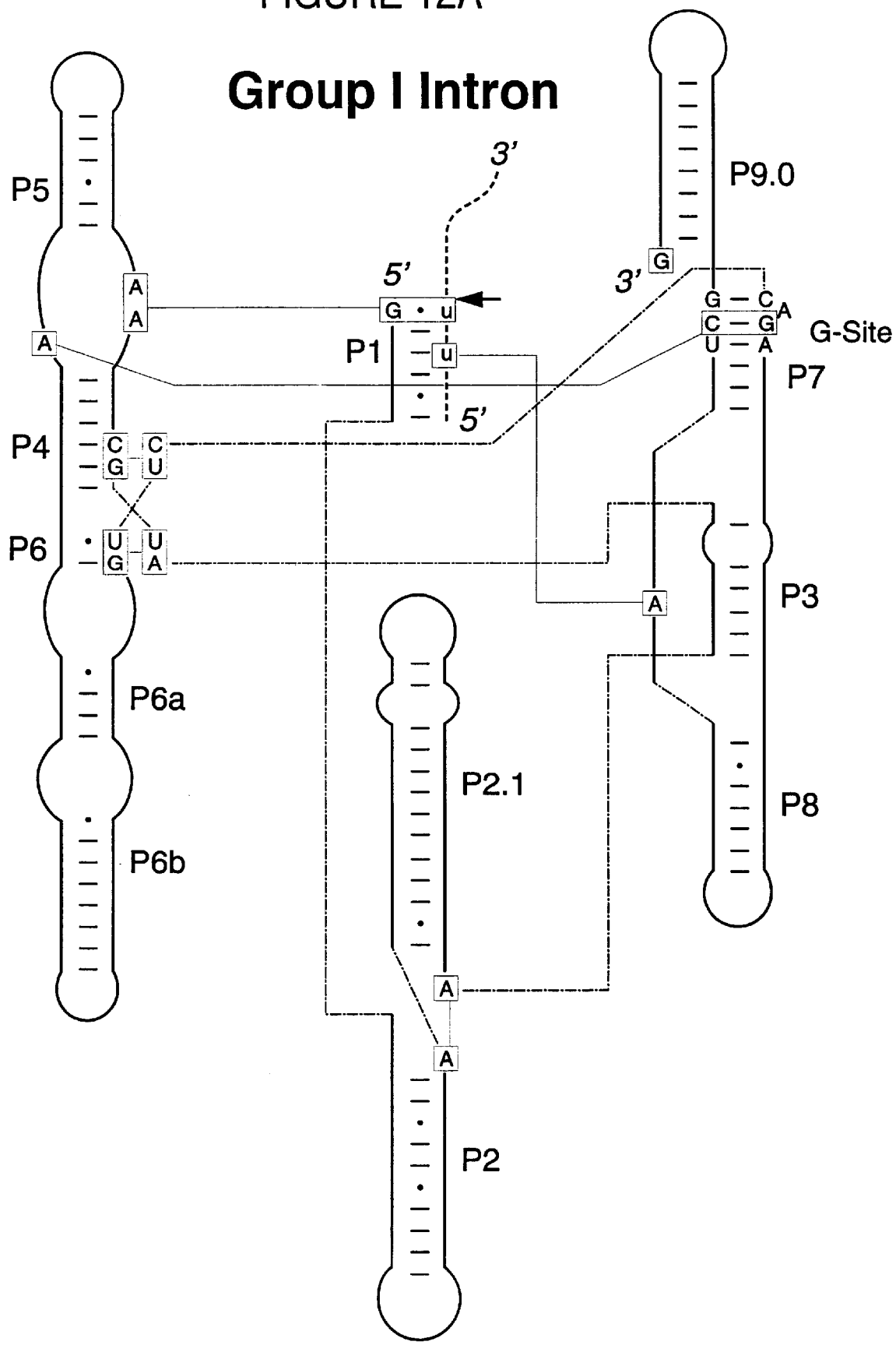
Figure 12B:
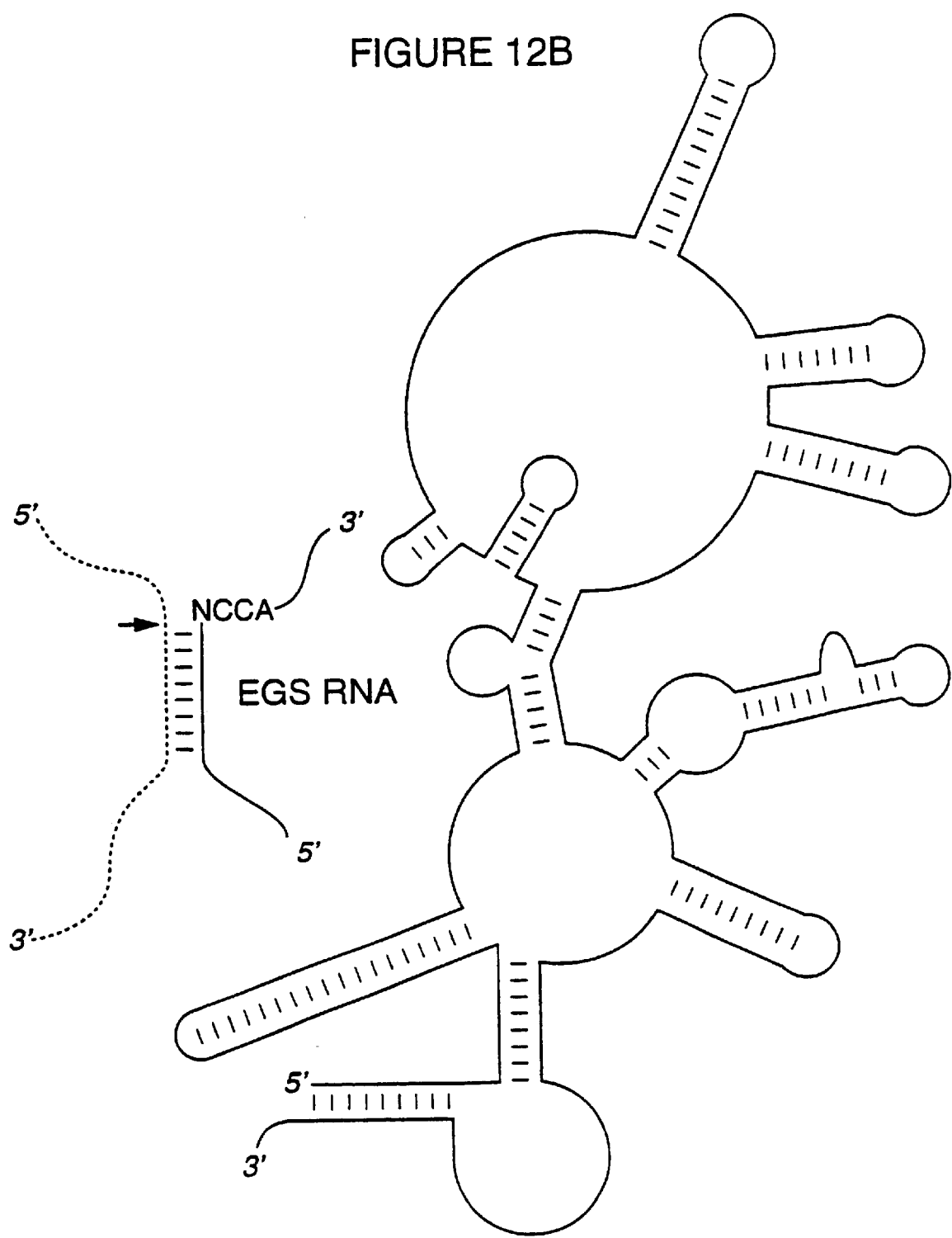
Figure 12C:
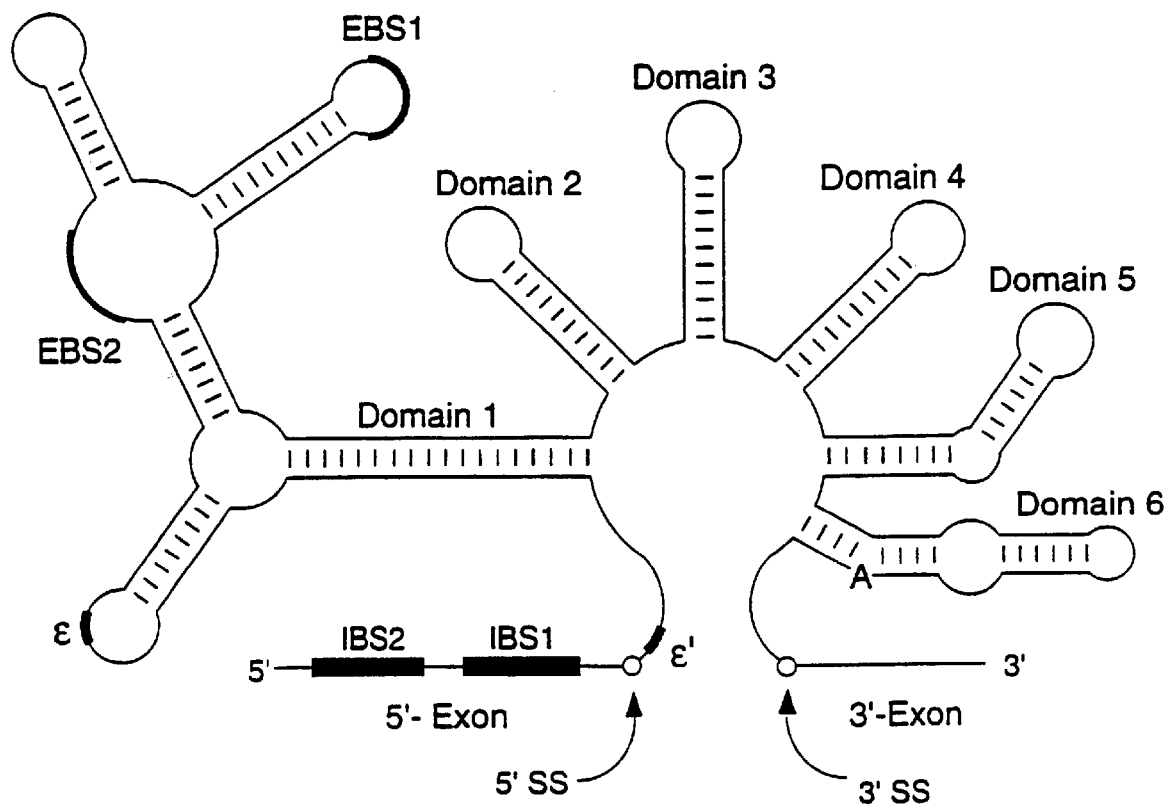
Figure 12D:
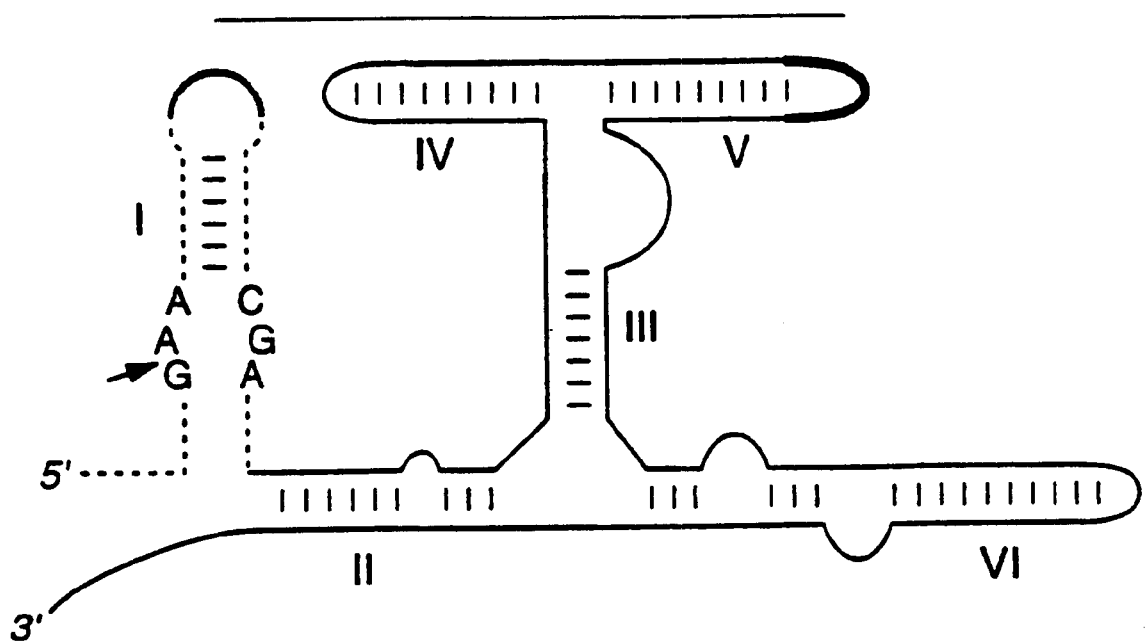
Figure 12E:
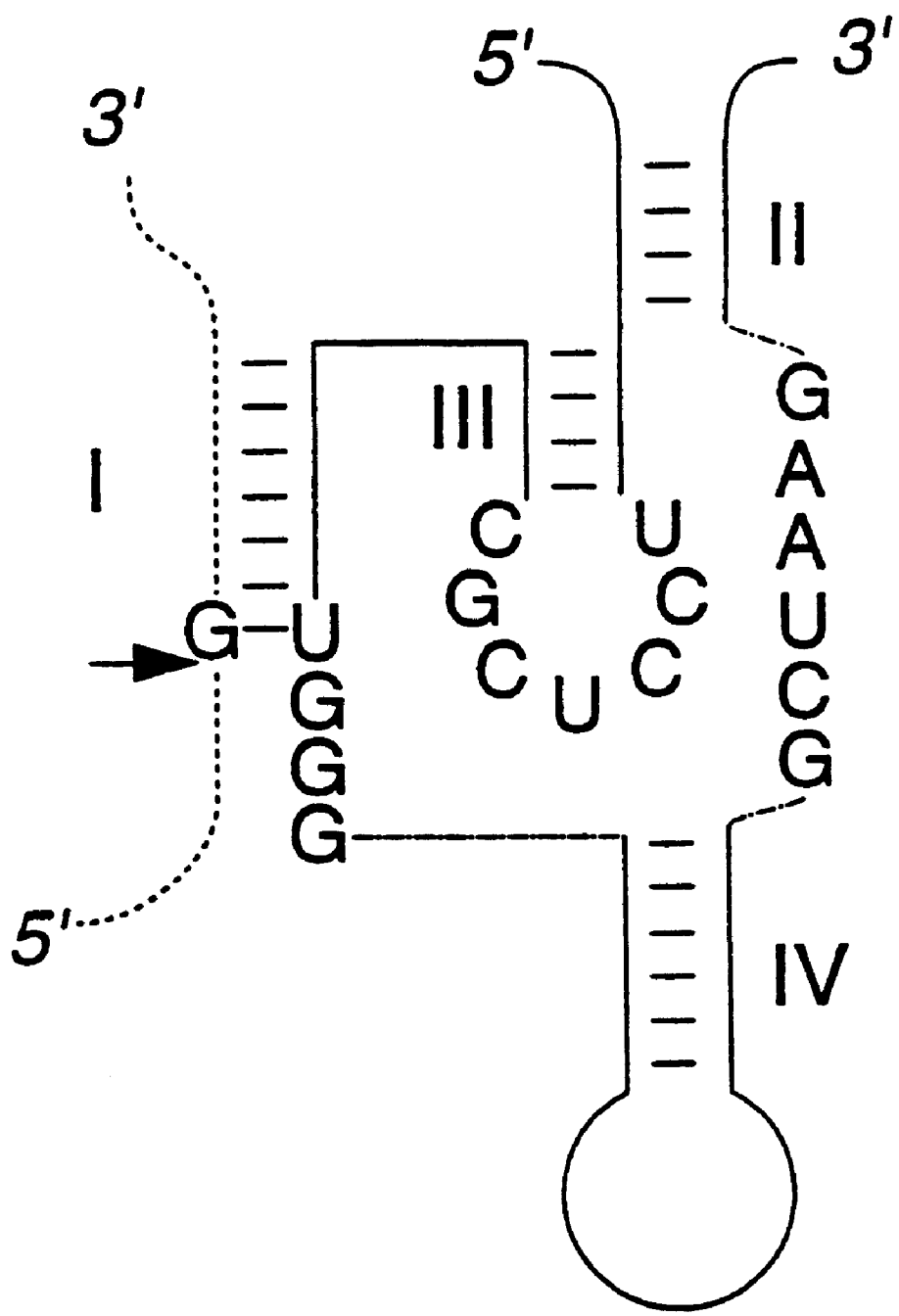
Figure 12F:
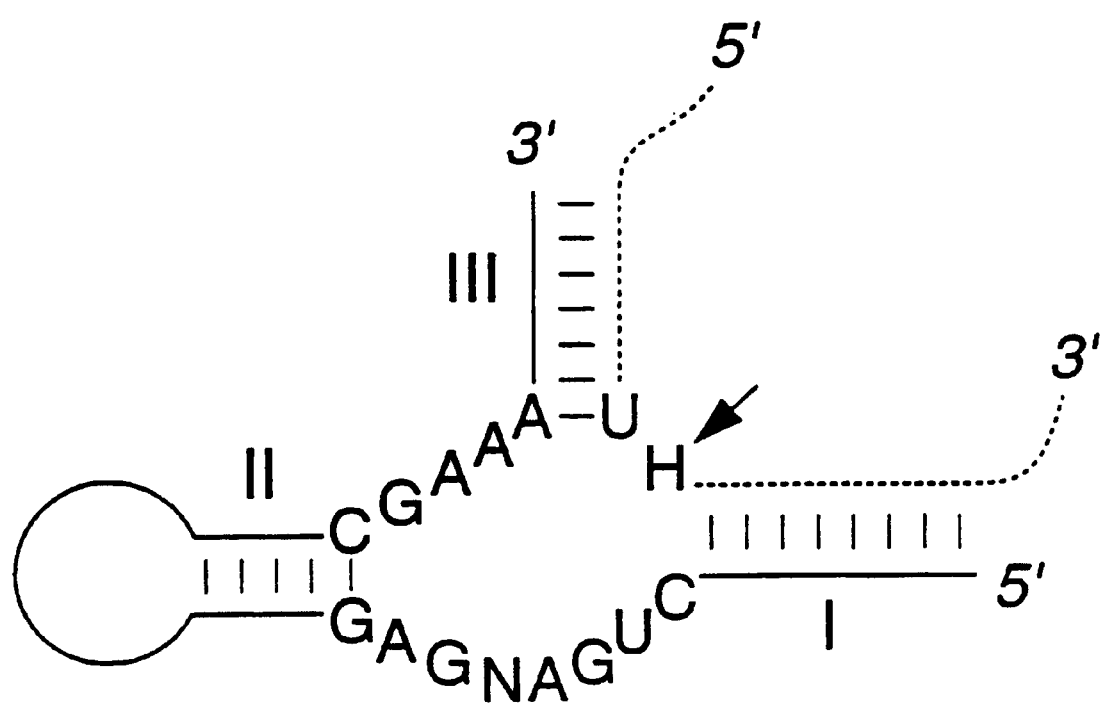
Figure 12G:
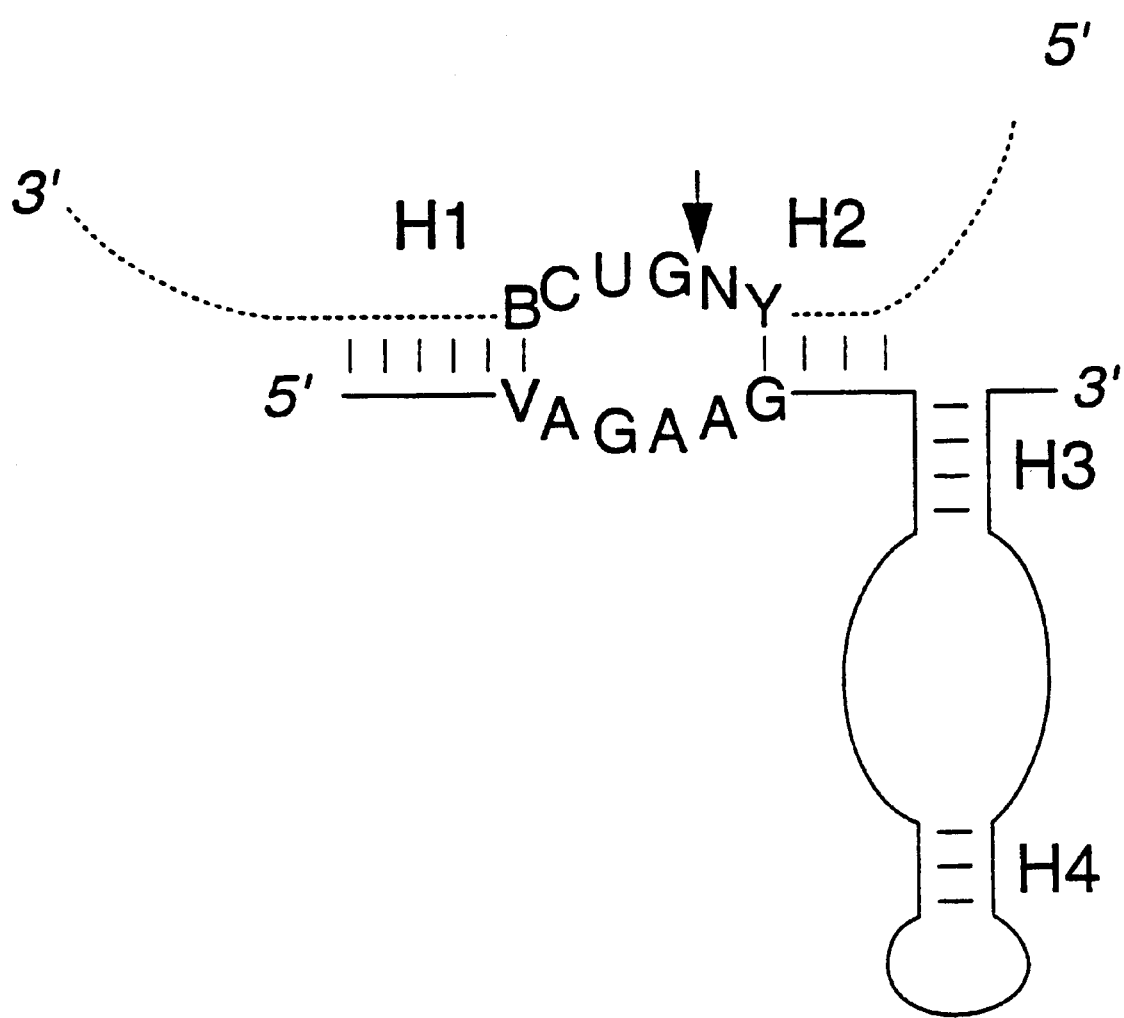
Figure 14:
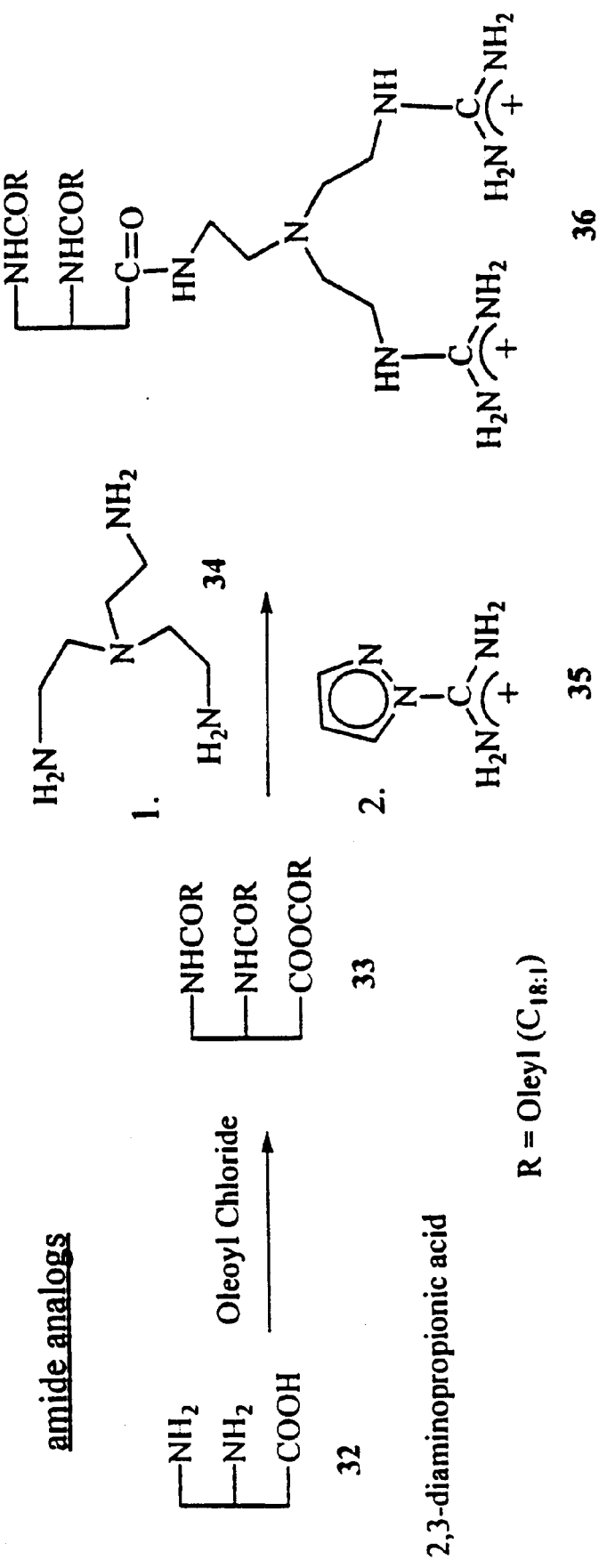

FIG. 14 depicts a scheme for the synthesis of N$_2$,N$_3$-dioleyl-(N,N'-diguanidinoethyl- aminomethane)-2,3-diaminoproprioric acid.

FIG. 15 depicts a graphical representation of a blood clearance study over time for an EPC:CHOL:DOTAP:DSPE-PEG$_{2000}$ liposome encapsulated ribozyme. The concentration of in fact ribozyme was measured in the plasma of 3 mice per group at the following time points: 15 minutes, 1 hour, 4 hours, and 24 hours.

Cationic lipids are bifunctional reagents (cationic head group conjugated to a lipid tail) that include a positively charged group that can ion-pair with an anionic group present in a negatively charged polymer, such as a phosphate group present in a nucleic acid phosphodiester linkage or a phosphorothioate group present in nucleic acid having a modified phosphodiester linkage. Preferably, the cationic group ion-pairs with a negatively charged polymer to form a lipid:polymer complex, such as a complex with a polynucleotide or a polyaminoacid (e.g. RNA, DNA, and protein). More preferably, the cationic group ion-pairs with RNA having enzymatic activity, such as a ribozyme. Formation of the ion-pair increases the intrinsic hydrophobicity of the negatively charged polymer and facilitates diffusion of the polymer across a cell membrane into the cell. The lipid:polymer complex can contain more than one lipid molecule. Preferably, a lipid:polymer complex contains lipid in an amount to ion-pair with at least 50% of the anionic groups of a negatively charged polymer. More preferably, a lipid:polymer complex contains lipid in an amount to ion-pair with at least 90% of the anionic groups of a negatively charged polymer. The lipid of an lipid:polymer complex can be the same or different. For example, the complex can contain lipids differing in the cationic groups. The amount of cationic lipid and negatively charged polymer which should be combined to achieve the desired amount of ionic pairing depends on the environment in which the lipid and the polymer is mixed, the type of lipid, and the type of polymer. The degree of ionic pairing can be measured by techniques known in the art (see, for example, U.S. Pat. No. 5,583,020, the contents of which are incorporated by reference herein). As a general guideline, the lipid molecule should be provided in an amount of at least two to ten times per negative charge on the polymer molecule.

Cationic lipids represent a subset of compounds in the broader class of multidomain cellular transport vehicles (MCTVs). The MCTV family of the invention includes single compounds as well as multi-component delivery systems that incorporate structural domains designed to improve membrane permeability, cellular targeting, while reducing the nonspecific interactions and toxicity of the incoming compound. In addition to cationic lipids, examples of MCrvs include transporters such as facial amphiphiles and other amphipathic compounds, carriers with targeting elements such as glycated moieties, peptides and vitamins, and liposomes with fasogenic elements, pegylated lipids, and/or pH-sensitive components.

By "nucleic acid molecule" as used herein is meant a molecule having nucleotides convalently linked to each other and in the general size range of 2 nucleotide bases up to 100 kilobases or more, preferably in the size range of 10 bases up to 50 kb, and preferably in the size range of 100 bases up to 10 kb and most preferably in the size range of 1 kb up to 5 kb. The nucleic acid can be single, double or multiple stranded and may comprise modified or unmodified nucleotides or non-nucleotides or various mixtures and combinations thereof. Non-limiting examples of nucleic acid molecules according to the invention are ribozymes, plasmid DNA, antisense oligonucleotides, 2-5A antisense chimera, triplex forming oligonucleotides, peptide nucleic acid molecules, nucleotides and others.

By "oligonucleotide" or "polynucleotide" as used herein, is meant a molecule comprising two or more nucleotides covalently linked.

By "ribozyme" is meant a nucleic acid molecule capable of catalyzing (altering the velocity and/or rate of) a variety of reactions including the ability to repeatedly cleave other separate nucleic acid molecules (endonuclease activity) in a nucleotide base sequence-specific manner. Such a molecule with endonuclease activity may have complementarity in a substrate binding region to a specified gene target, and also has an enzymatic activity that specifically cleaves RNA or DNA in that target That is, the nucleic acid molecule with endonuclease activity is able to intramolecularly or intermolecularly cleave RNA or DNA and thereby inactivate a target RNA or DNA molecule. This complementarity functions to allow sufficient hybridization of the enzymatic RNA molecule to the target RNA or DNA to allow the cleavage to occur. 100% complementarity is preferred, but complementarity as low as 50–75% may also be useful in this invention. The nucleic acids may be modified at the base, sugar, and/or phosphate groups. The term enzymatic nucleic acid is used interchangeably with phrases such as ribozymes, catalytic RNA, enzymatic RNA, catalytic DNA, catalytic oligonucleotides, nucleozyme, DNAzyme, Enzymatic DNA, RNA enzyme, endoribonuclease, endonuclease, minizyme, leadzyme, oligozyme or DNA enzyme. All of these terminologies describe nucleic acid molecules with enzymatic activity. The specific enzymatic nucleic acid molecules described in the instant application are not limiting in the invention and those skilled in the art will recognize that all that is important in an enzymatic nucleic acid molecule of this invention is that it has a specific substrate binding site which in the case of an endonuclease has sequences complementary to one or more of the target nucleic acid regions, and that it have nucleotide sequences within or surrounding that substrate binding site which impart a catalytic activity to the molecule.

By "enzymatic portion" or "catalytic domain" is meant that portion/region of the ribozyme essential for catalyzing a reaction such as cleavage of a nucleic acid substrate.

By "substrate binding arm" or "substrate binding domain" is meant that portion/region of a ribozyme which interacts with the substrate, such as able to base-pair with a portion of a nucleic acid substrate that is complementary. Generally, such complementarity is 100%, but can be less if desired. For example, as few as 10 bases out of 14 may be base-paired. Such arms are shown generally in FIG. 12 and Table I. That is, these arms contain sequences within a ribozyme which are intended to bring ribozyme and target together through complementary base-pairing interactions. The ribozyme of the invention may have binding arms that are contiguous or non-contiguous and may be varying lengths. The length of the binding arm(s) are preferably greater than or equal to four nucleotides; specifically 12– 100 nucleotides; more specifically 14–24 nucleotides long. If a ribozyme with two binding arms are chosen, then the length of the binding arms are symmetrical (i.e., each of the binding arms is of the same length; e.g., six and six nucleotides or seven and seven nucleotides long) or asymmetrical (ie., the binding arms are of different length; e.g., six and three nucleotides or three and six nucleotides long).

By "complementarity" as used herein is meant a nucleic acid that can form hydrogen bond(s) with other nucleic acid sequence by either traditional Watson-Crick or other non-traditional types (for example, Hoogsteen type) of base-paired interactions.

By "antisense" it is meant a non-enzymatic nucleic acid molecule that binds to target RNA by means of RNA-RNA or RNA-DNA or RNA-PNA (protein nucleic acid; Egholm et al., 1993 *Nature* 365, 566) interactions and alters the activity of the target RNA (for a review see Stein and Cheng, 1993 *Science* 261, 1004).

By "2-5A antisense chimera" it is meant, an antisense oligonucleotide containing a 5' phosphorylated 2'-5'-inked adenylate residues. These chimeras bind to target RNA in a sequence-specific manner and activate a cellular 2-5A-dependent ribonuclease which, in turn, cleaves the target RNA (Torrence et al., 1993 *Proc. Natl. Acad. Sci. USA* 90, 1300).

By "triplex forming oligonucleotides (TFO)" it is meant an oligonucleotide that can bind to a double-stranded DNA in a sequence-specific manner to form a triple-strand helix. Formation of such triple helix structure has been shown to inhibit transcription of the targeted gene (Duval-Valentin et al., 1992 *Proc. Natl. Acad. Sci. USA* 89, 504).

The "biological system" as used herein may be a eukaryotic system or a prokaryotic system, may be a bacterial cell, plant cell or a mammalian cell, or may be of plant origin, mammalian origin, yeast origin, Drosophila origin, or archebacterial origin.

By "cation" is meant a positively charged molecule.

By "vitamin" is meant a small molecule, such as riboflavin, nicotinamide, biotin, thiamine, lipoic acid, retinal, pyridoxal, folate, pantothenic acid, cyanocobalamin, aminopterin, and their respective analogs, which bind to a specific protein and participate directly in enzyme catalysis.

Method of Use

The cationic lipid molecules of the instant invention can be used to administer negatively charged polymers which act as pharmaceutical agents. Pharmaceutical agents prevent, inhibit the occurrence, or treat (alleviate a symptom to some extent, preferably all of the symptoms) of a disease state in a patient.

By "patient" is meant an organism which is a donor or recipient of explanted cells or the cells themselves. "Patient" also refers to an organism to which the compounds of the invention can be administered. Preferably, a patient is a mammal, e.g., a human, primate or a rodent.

Generally, these molecules are used in solution with the negatively charged polymer to be administered (e.g., RNA, DNA or protein) and introduced by any standard means, with or without stabilizers, buffers, and the like, to form a pharmaceutical composition. When it is desired to use a liposome delivery mechanism, standard protocols for formation of liposomes can be followed. The compositions of the present invention may also be formulated and used as tablets, capsules or elixirs for oral administration; suppositories for rectal administration; sterile solutions; suspensions for injectable administration; and the like.

The present invention also includes pharmaceutically acceptable formulations of the compounds described above, preferably in combination with the negatively charged polymer to be delivered. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic administration, into a cell or patient, preferably a human. Suitable forms, in part, depend upon the use or the route of entry, for example oral, transdermal, or by injection. Such forms should not prevent the composition or formulation to reach a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

By "systemic administration" is meant in vivo systemic absorption or accumulation of drugs in the blood stream followed by distribution throughout the entire body. Administration routes which lead to systemic absorption include, without limitations: intravenous, subcutaneous, intraperitoneal, inhalation, oral, intrapulmonary and intramuscular. Each of these administration routes expose the desired negatively charged polymers, e.g., nucleic acids, to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful. This approach may provide enhanced delivery of the drug to target cells by taking advantage of the specificity of macrophage and lymphocyte immune recognition of abnormal cells, such as the cancer cells.

In a preferred embodiment, the invention features the use of the cationic lipids of the invention in a composition comprising surface-modified liposomes containing poly (ethylene glycol) lipids (PEG-modified, or long-circulating liposomes or stealth liposomes). These formulations offer an method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601–2627; Ishiwata et al., *Chem. Pham. Bull.* 1995, 43, 1005–1011). Such liposomes have been shown to accumulate selectively in tumors, presumably by extravasation and capture in the neovascularized target tissues (Lasic et al., *Science* 1995, 267, 1275–1276; Oku et al., 1995, *Biochim. Biophys. Acta,* 1238, 86–90). The long-circulating liposomes enhance the pharmacokinetics and pharmacodynamics of DNA and RNA, particularly compared to conventional cationic liposomes which are known to accumulate in tissues of the MPS (Liu et al., *J. Biol. Chem.* 1995, 42, 24864–24870; Choi et al., International PCT Publication No. WO 96/10391; Ansell et al., International PCT Publication No. WO 96/10390; Holland et al., International PCT Publication No. WO 96/10392; all of these are incorporated by reference herein). Long-circulating liposomes are also likely to protect drugs from nuclease degradation to a greater extent compared to cationic liposomes, based on their ability to avoid accumulation in metabolically aggressive MPS tissues such as the liver and spleen. All of these references are incorporated by reference herein.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences,* Mack Publishing Co. (A. R. Gennaro edit. 1985) hereby incorporated by reference herein. For example, preservatives, stabilizers, dyes and flavoring agents may be provided. Id. at 1449. These include sodium benzoate, sorbic acid and esters of p-hydroxybenzoic acid. In addition, antioxidants and suspending agents may be used. Id.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors which those skilled in the medical arts will recognize.

Generally, an amount between 0.1 mg/kg and 100 mg/kg body weight/day of active ingredients is administered dependent upon potency of the negatively charged polymer.

The examples provided herein illustrate different aspects and embodiments of the present invention. Although the examples presented here primarily pertain to delivery of ribozymes and plasmid DNA, one skilled in the art will recognize that any nucleic acid, protein, lipid, or another molecule, either alone or in combinations can be delivered to target biological system using the teachings of the present invention. These examples are not intended in any way to limit the disclosed invention.

EXAMPLE 1
Synthesis of Diaminobutyric Acid and Guanidinium-based Cationic Lipids (FIG. 2)

Synthesis of palmityloleylamine (1)

1-bromohexadecane (15.27 g, 50 mmol) was rapidly added to oleylamine (26.75 g, 100 mmol) at 100° C. The reaction mixture was heated at 120° C. for 30 minutes and than cooled to room temperature. Chloroform(200 ml) was added followed by 1 N NaOH (50 ml). The mixture was then extracted with $H_2O$ (200 ml), the organic layer dried ($Na_2SO_4$) and concentrated to a syrup. Silica gel column chromatography using 5– 20% gradient methanol in dichloromethane afforded 20.5 g of palmityloleylamine as a syrup (yield, 83%). The identity of the product was confirmed using NMR spectroscopy. $^1$H NMR ($CDCl_3$) d 5.34 (m, 2H, CH=CH), 2.58 (m, 4H), 2.00 (m, 4H), 1.47 (m, 4H), 1.25 (m, 48H), 0.86 (m, 6H). FAB-MS: 493 $[M+H]^+$. (Other reagents could include oleyl-bromide and hexadecane amine)

Synthesis of N'-palmityl-N'-oleyl-N-CBZ-glycinamide (2)

(1) (2.46 g, 5 mmol) was added to a solution of N-CBZ-glycine N-hydroxysuccinimide ester (3.06 g, 10 mmol) suspended in dichloromethane (1.39 ml) containing triethylamine (TEA)(10 mmol). The reaction mixture was stirred at room temperature overnight and then concentrated to an oil under vacuum. Silica gel chromatography using 1–5% gradient methanol in dichloromethane gave 1.54 g of N'-palmityl-N'-oleyl-N-CBZ-glycinamide (yield, 45%). $^1$H NMR ($CDCl_3$) d 7.35 (m, phenyl), 5.83 (br s, NH), 5.35 (m, CH=CH), 5.12 (s, 2H, $CH_2Ph$), 4.00 (m, 2H, glycyl), 3.31 (m, 2H), 3.13 (m, 2H), 2.00 (m, 4H), 1.53 (m, 4H), 1.25 (m, 48H), 0.88 (m, 6H).

Synthesis of N'-palmityl-N'-oleyl-glycinamide (3)

10% Palladium on Carbon (Pd/C) was added to N'-palmityl-N'-oleyl-N-CBZ-glycinamide (0.5 g, 0.73 mmol) dissolved in absolute ethanol (3 ml) under argon gas. The flask was immersed in a 20° C. water bath prior to the addition of 1,4-cyclohexadiene (0.66 ml). The reaction mixture was stirred at room temperature overnight, the catalyst was filtered off and the filtrate evaporated to dryness giving 0.3 g of product (yield, 75%). $^1$H NMR (acetone-$d_6$) d 5.41 (m, 2H, CH=CH), 4.07 (br s, 2H, glycyl), 3.36 (m, 2H), 3.29 (m, 2H), 2.80 (br s, $NH_2$), 2.05 (m, 2H), 1.98 (m, 2H), 1.63 (m, 2H), 1.25 (m, 48H), 0.87 (m, 6H). FAB-MS: 549 $[M+H]^+$.

Synthesis of N'-palmityl-N'-oleyl-alpha,gamma-bis-Boc-diaminobutyryl-glycinamide (4)

The mixture of 3 (1.12 g, 2.04 mmol), N-alpha-N-gamma-di-Boc-diaminobutyric acid (631 mg, 2.24 mmol), 2-ethoxy-1-ethoxycarbonyl-1,2-dihydroquinoline (EEDQ) (553 mg, 2.24 mmol) in $CH_2Cl_2$ was stirred for 1 hour at room temperature. The mixture was then concentrated to a syrup and 1.2 g of the product was isolated by column chromatography using 20–50% gradient of hexanes in ethyl acetate (yield, 69%). $^1$H NMR ($CDCl_3$) d 7.14 (br s, NH), 5.38 (m, 2H, CH=CH), 5.28 (br s, 1H, NH), 5.12 (br s, 1H, NH), 4.02 (m, 2H, glycyl), 3.42 (m, 1H), 3.31 (m, 2H), 3.15 (m, 2H), 3.02 (m, 2H), 1.95 (m, 4H), 1.77 (m, 2H), 1.53 (m, 4H), 1.25 (m, 48 H). FAB-MS: 850 $[M+H]^+$.

Synthesis of N'-palmityl-N'-oleyl-alpha,gamma-diaminobutyryl-glycinamide (JA59311)(5)

Compound 4 (350 mg, 0.41 mmol) was dissolved in dioxane (6 ml) followed by the addition of 4 M HCl in dioxane (6 ml). The reaction mixture was stirred at room temperature for 2 hours, than concentrated in vacuo and azeotroped twice with toluene. The residue was partitioned between $CH_2Cl_2$ and 0.2 N NaOH, the organic layer was washed with saturated $NaHCO_3$ solution, and then dried ($Na_2SO_4$) and evaporated to dryness. Flash silica gel chromatography using $CH_2Cl_2$/methanol/conc. $NH_4OH$ 40:10:2 yielded 200 mg of compound 5 (yield, 75%). $^1$H NMR ($CDCl_3$) d 8.06 (br s, 1H, NH), 5.38 (m, 2H, CH=CH), 4.04 (m, 2H, glycyl), 3.54 (m, 1H), 3.31 (m, 2H), 3.17 (m, 2H), 2.86 (m, 2H), 1.93 (m, 4H), 1.67 (m, 2H), 1.54 (m, 4H), 1.41 (br s, 4H, $NH_2$), 1.25 (m, 48H), 0.87 (m, 6H). FAB-MS: 650 $[M+H]^+$.

Synthesis of N'-palmityl-N'-oleyl-N-gamma-carboxamidine-alpha,gamma-diaminobutyryl-glycinamide (JA59312) (6)

To the solution of 5 (0.16 g, 0.25 mmol) and diisopropylethylamine (DIPEA) (83 mL) in THF/methanol 1:1 (0.8 ml), 1H-pyrazole-1-carboxamidine hydrochloride (70 mg, 0.48 mmol) was added under argon gas. The reaction mixture was stirred at room temperature overnight and then concentrated to a syrup. Silica gel column chromatography using $CH_2Cl_2$ followed by $CH_2Cl_2$/methanol/conc. $NH_4OH$ 40:10:2 yielded 50 mg of compound 6 (yield, 29%). $^1$H NMR ($CDCl_3$) d 5.37 (m, 2H, CH=CH), 4.07 (m, 2H, glycyl), 3.94 (m, 1H), 3.42 (m, 2H), 3.21 (m, 4H), 2.01 (m, 6H), 1.58 (m, 4H), 1.46 (m, 2H, $NH_2$), 1.25 (m, 48H), 0.87 (m, 6H). FAB-MS: 692 $[M+H]^+$.

Synthesis of N'-palmityl-N'-oleyl-alpha,gamma-bis-trimethylammoniumbutyryl-glycinamide (JA59316)(7)

A dihydrogenchloride salt of 5 (130 mg, 0.2 mmol) was dissolved in methanol (4 ml) and combined with $KHCO_3$ (0.2 g) and $CH_3I$ (0.2 ml). The mixture was then stirred at room temperature for 3 days. The reaction mixture was then filtered through the bed of Celite, followed by filtration through 0.45 m PTFE filter. The filtrate was then evaporated to dryness affording 160 mg of the desired product (yield, 94%). $^1$H NMR ($CDCl_3$) d 3.58 [s, 9H, $(CH_3)_3$], 3.44 [s, 9H, $(CH_3)_3$].

Synthesis of N'-palmityl-N'-oleyl-N-carboxamidine-glycinamide.HCl (JA59314)(8)

Using the same procedure described above for the preparation of 6 except that crystallization from methanol instead of column chromatography was used for purification, 8 was prepared in 51% yield. $^1$H NMR ($CDCl_3$) d 7.70–7.25 (m, 5H, NH), 5.38 (m, 2H, CH=CH), 4.25 (m, 2H, glycyl), 3.27

(m, 4H), 1.96 (m, 4H), 1.53 (m, 4H), 1.25 (m, 48 H), 0.87 (m, 6H). FAB-MS: 592 [M+H]+.

Synthesis of N'palmityl-N'-oleyl-guanidine (JA59317) (9)

The mixture of a hydrochloride salt of 1 (285 mg, 0.54 mmol), cyanamide (50 mg, 1.19 mmol) and 1-butanol (2 ml) was stirred at 120° C. for 2 hours. The cooled mixture was diluted with $CH_2Cl_2$(50 ml) and washed with saturated aqueous NaCl(Brine)/methanol 1:1 (50 ml). The organic layer was then dried ($Na_2SO_4$), evaporated to an oil and chromatographed on a column of silica gel using $CH_2Cl_2$/methanol/conc. $NH_4OH$ 40:10:2 giving 80 mg of the desired material (yield, 28%). $^1H$ NMR ($CDCl_3$) d 7.08 (br s, 1H, NH), 5.34 (m, 2H, CH=CH), 3.29 (m, 4H), 2.00 (m, 4H), 1.62 (m, 4H), 1.25 (m, 48H), 0.88 (m, 6H). FAB-MS: 535 [M+H]+.

EXAMPLE 2
Synthesis of DS 46596 (12)

Synthesis of Cholesterylamine (10)

Referring to FIG. 3, cholesteryl chloride (10 grams, 25 mmol) was partially dissolved in dry methanol (50 ml) and the solution was heated with stirring to 155° C. for 18 hr at 500 psig using a 300 ml Parr bomb apparatus charged with dry ammonia gas. The bomb was cooled to room temperature and the methanol was removed by steam distillation on a rotary evaporator. Compound 10 was purified using E. Merck silica chromatography by eluting with dichloromethane/methanol (4:1 v/v) to yield 4 grams of the ninhydrin positive product (yield, 60%). Identity was confirmed by ES-MS.

Synthesis of $Boc_3$arginineNHcholesterylamide (11)

A 200 mL pear shaped flask with stir bar was charged with a mixture of 10 (1 g, 2.6 mmol), $Boc_3$ arginine (1.2 grams, 2.6 mmol), diisopropylcarbodiimide (450 ul, 2.9 mmol) and dichloromethane (70 mls). The mixture of reagents was stirred at room temperature for two hours. Following the reaction, the solution was washed with aqueous sodium bicarbonate (5% w/v) and the organic layer was separated and dried to a solid using a rotary evaporator. Compound 11 was dissolved in 5 mls of dichloromethane prior to purification using silica gel chromatography. (yield, 90%). Identity was confirmed by ES-MS. $^1H$ NMR (dmso-d6):. $^1H$ NMR (dmso-d6): 9.32 (bd), 6.63 (d), 5.30 (m), 4.00 (m), 3.80 (m) 3.40 (m), 1.539 (s, tBoc), 1.517 (s, tBoc), 1.497(s, tBoc).

Synthesis of Boc arginineNHcholesterylamide (DS4659) (12)

Compound 11 (50 mg, 60 umol) was dissolved in anhydrous 1,4-dioxane (300 ul) and combined with 4M HCl in dioxane (400 ul). The mixture was left at room temperature for 2 hours and the reaction was stopped by removing all solvent and HCl using a stream of dry nitrogen gas. Compound 12 was isolated using a wide pore C18 silica column and an isocratic methanol: water (88:12) eluant with detection at 210 nm. Fractionation allowed recovery of 20 mgs of compound 12 (yield, 44%). Identity was confirmed by ES-MS. $^1H$ NMR (dmso-d6): 7.82 (d), 6.36 (bs), 3.51 (m), 3.43 (m), 3.33 (m) 3.15 (m), 1.472 (s, tBoc).

EXAMPLE 3
Synthesis of PH 55933 (15) and PH 55938 (16)

Synthesis of (13)

Referring to the FIG. 4, to a solution of methylphosphonic dichloride (0.332 g, 2.5 mmol, $^{31}P$ NMR s, 43.93 ppm) stirring at room temperature under positive pressure argon was added 4-dimethylaminopyridine(DMAP) (0.31 g, 2.5 mmol). The resulting clear, colorless solution was cooled to −70° C. and a solution of cholesterol (0.97 g, 2.5 mmol) suspended in anhydrous dichloromethane (20 ml) was added via syringe with vigorous stirring over a period of one hour. The reaction mixture was allowed to warm to room temperature and was maintained at room temperature for 18 hours at which time $^{31}P$ NMR analysis of a small aliquot of the reaction mixture indicated complete reaction (d, 39.08 ppm).

Crude (13) was treated with additional DMAP (0.31 g, 2.5 mmol) and the reaction mixture cooled to −70° C. while stirring under positive pressure argon. H-Lys(Z)—$OCH_3$ (0.66 g, 2.25 mmol) in anhydrous dichloromethane (20 ml) was added dropwise via syringe over a period of one hour. The reaction mixture was warmed to room temperature and stirred for an additional 18 hours (reaction complete by $^{31}P$ NMR). Direct loading onto flash silica followed by a gradient of 0 to 10% EtOAc/hexanes then 5% EtOH/diclhloromethane gave 1.12 g of (14) (Yield, 60% over two steps). $^{31}P$ NMR (s, 30.98 ppm).

Synthesis of Cholesterol-Lysine-methylphosphonoamidate (PH55933) (15)

Compound (14) (1.0 g, 1.35 mmol) was dissolved in anhydrous EtOH and cooled to 0° C. with an ice/water bath while stirring under argon. 10 Pd/c (1.0 g, 1 mass eq.) was added to the reaction mixture followed by dropwise addition of 1,4 cyclohexadiene (1.27 ml, 13.5 mmol). After warming to room temperature, the reaction was complete after 4 hours as determined by TLC (15% MeOH/dichloromethane). The reaction mixture was filtered over celite and dried in vacuo. Flash chromatography utilizing a gradient of 5 to 15% MeOH/dichloromethane 1% TEA afforded 0.64 g of (15): (yield, 78%) $^{31}P$ NMR (s, 30.88 ppm), mass spec. calcd=606.87, found=607.47.

Synthesis of Cholesterol-Homoarginine-methylphosphonoamidate (PH55938) (16)

To a solution of (15) (0.131 g, 0.216 mmol) stirring at room temperature under argon in anhydrous DMF (2.0 ml), 1-H-pyrazole-1-carboxamidine. HCl (32 mg, 0.216 mmol) was added followed by diisopropylethylamine (28 ml, 0.216 mmol). The reaction mixture was stripped slightly on a rotovap then rotated overnight without vacuum at room temperature. After removing DMF in vacuo the reaction residue was dissolved in dichloromethane and applied to a flash silica gel column. An isocratic system of 20% MeOH/dichloromethane, 2% $NH_4OH$ followed by treatment with Dowex OH− (300 mg) in MeOH gave 80 mg of desired product (yield, 57%). P NMR (s, 31.99 ppm), mass spec. calcd=648.91, found=649.48.

EXAMPLE 4
Synthesis of PH 55939 (17)

Synthesis of Cholesterol-Lysine-methylphosphonoamidate amide (PH55939) (17)

Refering to FIG. 5, compound (15) (76 mg, 0.125 mmol) was treated with a 0° C. saturated methanolic ammonia solution (5 ml) at room temperature for 18 hours (some venting required). The reaction mixture was evaporated in vacuo then purified by flash silica gel chromatography to give 45 mg of product (yield,61%). $^{31}$P NMR (s, 32.17 ppm), mass spec. calcd=591.86, found=592.23.

EXAMPLE 5
Synthesis of PH 55941 (18) and PH 55942 (19)

Synthesis of Cholesterol-TREN-methylphosphonamidate (PH55941) (18)

Refering to FIG. 6, 4-Dimethylaminopyridine (DMAP) (0.31 g, 2.5 mmol) was added to a solution of methylphosphonic dichloride (0.332 g, 2.5 mmol, $^{31}$P NMR s, 43.93 ppm) stirring at room temperature under positive pressure argon gas. The resulting clear, colorless solution was cooled to −70° C. and a solution of cholesterol (0.97 g, 2.5 mmol) in anhydrous dichloromethane (20 ml) was added via syringe with vigorous stirring over a period of one hour. The reaction mixture was allowed to warm to room temperature and was maintained for 18 hours at which time $^{31}$P NMR analysis of a small aliquot of the reaction mixture indicated complete reaction (d, 39.08 ppm). Crude (13) was treated with additional DMAP (0.31 g, 2.5 mmol) and the reaction mixture cooled to −70° C. while stirring under positive pressure argon. Tris(2-aminoethyl)amine (TREN) (0.37 ml, 2.5 mmol) in anhydrous dichloromethane (20 ml) was added dropwise via syringe over a period of two hours. The reaction mixture was warmed to room temperature and stirred for an additional 18 hours (reaction complete by $^{31}$P NMR). Direct loading onto flash silica followed by a gradient of 10 to 20% MeOH/dichloromethane with 1 to 4% $NH_4OH$ gave 0.442 g of (18) as a white foam: (yield,28% over two steps), $^{31}$P NMR (d, 32.57 ppm), mass spec. calcd=592.89, found=593.49.

Synthesis of Cholesterol-TREN-bis-guanidinium methylphosponamidate (PH55942) (19)

Compound (18) (0.148 g, 0.25 mmol) was dissolved in anhydrous DMF (1.0 ml) and anhydrous dichoromethane (5.0 ml). 1-H-pyrazole-1-carboxamidine. HCl (73 mg, 0.50 mmol) was added to the reaction mixture followed by diisopropylethylamine (87 ml, 0.50 mmol). Dichloromethane was stripped off of the reaction mixture on a rotovap then rotation continued overnight without vacuum at room temperature. After removing DWF in vacuo the reaction residue was dissolved in dichloromethane and applied to a flash silica gel column. A gradient of 5 to 20% MeOH/dichloromethane with 0.5 to 2% $NH_4OH$ followed by treatment with Dowex OH⁻ (300 mg) in MeOH gave pure (19): 0.11 g, 65%, $^{31}$P NMR (d, 33.83 ppm), mass spec. calcd=676.97, found=677.54.

EXAMPLE 5
Synthesis of PH 55943

Synthesis of Cholesterol-Lysine-methylphosphonoamidate (PH55943) (20)

Refering to FIG. 7, crude (13) was treated with additional DMAP (0.31 g, 2.5 mmol) and the reaction mixture cooled to −70° C. while stirring under positive pressure argon. H-His(Bz1)OCH$_3$ (0.65 g, 2.5 mmol) in anhydrous dichloromethane (20 ml) was added dropwise via syringe over a period of one hour. The reaction mixture was then warmed to room temperature and stirred for 18 hours (reaction complete by $^{31}$P NMR). Direct loading onto flash silica followed by a gradient of 2 to 10% EtOAc/hexanes then 0 to 5% MeOH/dichloromethane gave 0.53 g of (20) (30% over two steps), $^{31}$P NMR (d, 31.39 ppm), mass spec. calcd=705.96, found=706.47.

EXAMPLE 6
Synthesis of PH 55945 (21)

Synthesis of Cholesterol-Histidine-methylphosphonamidate (PH55945) (21)

Refering to FIG. 8, crude (13) was treated with additional DMAP (0.31 g, 2.5 mmol) and the reaction mixture cooled to −70° C. while stirring under positive pressure argon. 1-(3-aminopropyl)-imidazole (0.30 ml, 2.5 mmol) in anhydrous dichloromethane (20 ml) was added dropwise via syringe over a period of one hour. The reaction mixture was warmed to rt and stirred at rt for an additional 18 hours (reaction complete by $^{31}$P NMR). Direct loading onto flash silica after saturated bicarb washing followed by a gradient of 0 to 10% EtOAc/hexanes then 0 to 10% MeOH/dichloromethane affording 0.77 g of (21): (yield, 54% over two steps), $^{31}$P NMR (d, 32.47 ppm), mass spec. calcd=571.82, found=572.33.

EXAMPLE 7
Synthesis of Vitamin B6 and Beta-alanine-based Cationic Lipids

Synthesis of N-CBZ-beta-Alanine N-hydroxysuccinimide ester (22)

Refering to FIG. 9, the compound was prepared according to Lewis et al. PNAS 1996, 93, 3176–3181 (incorporated by reference herein). Yield 80%. $^1$H NMR (DMSO-d$_6$) d 7.42 (t, 1H, NH), 7.33 (m, 5H, benzyl), 5.009 (s, CH$_2$), 1.47 (m, 4H), 3.32 (m, 2H, CH$_2$NH), 2.86 (t, 2H,CH$_2$CO), 2.79 (s, 4H, CH$_2$CH$_2$).

Synthesis of N'-palmityl-N'-oleyl-N-CBZ-beta-alanine amide (23)

Compound 22 (1.0 g, 2.03 mmol) was added to a solution of N-CBZ-beta-Alanine N-hydroxysuccinimide ester (0.16 g, 0.5 mmol) in CH$_2$C$_2$ containing Et$_3$N (0.42 ml, 3 mmol). The reaction mixture was stirred at room temperature overnight, diluted with dichloromethane and washed with saturated NaHCO$_3$ and brine. Organic layer was dried over sodium sulfate and evaporated to dryness. The residue was purified by flash chromatography on silica using mixture of EtOAc-Hexanes (1:3) as an eluent to give 1.32 g of 23 as a yellow oil(yield, 93%). $^1$H NMR (CDCl$_3$) d 7.34 (m, phenyl), 5.62 (t, NH), 5.35 (m, CH=CH), 5.082 (s, 2H, CH$_2$Ph), 3.49 (m, 2H, CH$_2$NH), 3.27 (m, 2H,), 3.15 (m, 2H), 2.5 (m, 2H, CH$_2$CO), 2.00 (m, 4H), 1.49 (m, 4H), 1.25 (m, 48H), 0.87 (m, 6H).

Synthesis of N'-palmityl-N'-oleyl-beta-alanine amide (AK 524-68) (POABA)(24)

Compound 23 (1.2 g, 1.72 mmol) was dissolved in absolute ethanol (10 ml) and 10% Pd—C was added under argon. The flask was then immersed in a 20° C. water bath prior to the addition of 1,4-cyclohexadiene (1.6 ml). The reaction mixture was stirred at room temperature for 40 hours, the catalyst was filtered off and the filtrate evaporated to dryness. The residue was purified by flash chromatography on silica eluting with the linear gradient of MeOH (5% to 10%) in dichloromethane to give 0.68 g, of 24 (yield, 70%). $^1$H NMR (CDCl$_3$) d 5.37 (m, 2H, CH=CH), 3.26 (m, 4H,), 3.16 (m, 2H), 2.75 (t, NH$_2$), 1.95 (m, 2H), 1.51 (m, 4H), 1.25 (m, 48H), 0.87 (m, 6H). FAB-MS: 563.6 [M+H]⁺.

Synthesis of N'-palmityl-N'-oleyl-N-carboxamidine-beta-alanine amide (AK 524-73) (GPPOA) (25)

The mixture of 24 (60 mg, 0.11 mmol), pyrazole carboxamidine hydrochloride (16 mg, 0.11 mmol) and diisopropylethylamine (20 mL, 0.12 mmol) in 0.5 mL of THF-MeOH (1:1) was stirred overnight at room temperature. It was then evaporated to dryness, dissolved in dichloromethane and washed with aqueous ammonia. The organic layer was dried over sodium sulfate to give 25 as an yellowish oil. Yield near quantitative. $^1$H NMR (CDCl$_3$) d 7.70–7.25 (m, 5H, NH), 5.38 (m, 2H, CH=CH), 3.43 (m, 2H, CH$_2$NH), 3.23 (m, 2H), 3.17 (m, 2H), 2.54 (m 2H, CH$_2$CO)1.96 (m, 4H), 1.49 (m, 4H), 1.25 (m, 48 H), 0.87 (m, 6H). FAB-MS: 605.6 [M+H]$^+$.

Synthesis of N(N"-palmityl-N"-oleyl-amidopropyl) pyridoxamine (AK 524-74) (POCAEP) (26): Compound 26 was prepared analogously to compound 27 (Yield, 78%). FAB-MS: 714.6 [M+H]$^+$.

EXAMPLE 8

Synthesis of AK524-76 (27)

N-cholesteryl-pyridoxamine (AK524-76) (CCAEP) (27)

Refering to FIG. 11, The suspension of Pyridoxal hydrochloride (0.1 g, 0.5 mmol) in ethanol was brought to pH 7 with 1N NaOH followed by the addition of aminocholesterol (0.19 g, 0.5 mmol). The pH of the resulting bright yellow solution was adjusted to 8 (1N NaOH) and set aside for 10 minutes. Sodium borohydride (20 mg, 0.5 mmol) was then added to the reaction mixture resulting in immediate color disappearance. After 15 minutes reaction mixture was acidified (pH 6) with 1N HCl, diluted with dichloromethane and washed with aqueous ammonia and water. The organic layer was dried over sodium sulfate and evaporated to dryness. The residue was purified by flash chromatography on silica using 10% MeOH in dichloromethane as an eluent to give 0.25 g (93%) of 27. $^1$H NMR (CDCl$_3$)d 7.78 (s, 1H, H-6 Pyr), 4.58 (s, 2H, CH$_2$O), 4.06 (AB-quartet 2H, CH$_2$N), 2.4 (s, 3H, 2-CH$_3$), 2.2–0.24 (m, cholesteryl moiety). FAB-MS: 537.4 [M+H]$^+$.

EXAMPLE 9

Synthesis of 2'-aminouridine-based Cationic Lipids

2'-Deoxy-2'-(N-Fmoc-beta-alanineamido) uridine (28)

Referring to FIG. 10, EEDQ (4.2 g, 17 mmol) was added to the solution of 2'-amino-2'-deoxy uridine (4 g, 16.45 mmol) and N-FMOC-beta-alanine (5.1 g, 16.45 mmol) in methanol and the reaction mixture was boiled for two hours. Subsequent flash chromatography on silica using a linear gradient of methanol (5% to 10% ) in dichloromethane afforded 6 g of 2'-Deoxy-2'-(N-Fmoc-beta-alanineamido) uridine (77%). $^1$H NMR (CDCl$_3$-DMSO-d6) d 10.398 (s, 1H, N3-H), 6.98–7.63 (m, H6, Fmoc), 6.16 (t, 1H, NHFmoc), 5.73 (d, 1H, H1', J$_{1',2'}$ 8.4), 5.34 (d, 1H, H5), 4.22 (m, 1H, 2'-H) 3.98 (dd 2H, CH$_2$), 3.88 (m, 1H, 3'-H), 3.77 (br s, 1H, 4'-H), 3.43 (m, 2H, 5'-CH$_2$), 3.1 (m, 2H, CH$_2$NHFmoc), 2.07 (t, 2H, CH$_2$CO).

Synthesis of 3',5'-Di-palmitoyl-2'-deoxy-2'-(N-Fmoc-beta-alanineamido) uridine (29)

Palmitoyl chloride (1.55 mL, 1.8 mmol) was added to a solution of nucleoside 28 in abs pyridine and the reaction mixture was stirred overnight at room temperature. The solution was then quenched with MeOH, evaporated to dryness, dissolved in dichloromethane and washed with saturated aq sodium bicarbonate and brine. The organic phase was dried over sodium sulfate and evaporated to dryness. The residue was purified by flash chromatography on silica (EtOAc-Hexanes 1:1) affording 0.5 g of 29 (yield, 65%).

Synthesis of 3',5'-Di-palmitoyl-2'-deoxy-2'-(beta-alanineamido) uridine (AK 524-71) (30)

To the solution of 29 (0.5 g, 0.49 mmol) in dichloromethane (5 mL) was added morpholine (1 mL) and the reaction mixture was stirred at room temperature for 36 hours. Subsequent flash chromatography on silica using linear gradient of methanol (5% to 10%) in dichloromethane afforded 0.22 g of desired product (yield, 56%) of 30 . FAB-MS: 791.6 [M+H]$^+$.

Synthesis of 3',5'-Di-palmitoyl-2'-deoxy-2'-(N-carboxamidine-beta-alanineamido) uridine (AK 524-75) (31)

Compound 31 was prepared analogously to compound 25. Yield 80%. FAB-MS: 833.6 [M+H]$^+$.

EXAMPLE 10

Preparation of Lipid-based Formulations Including Cationic Lipids and DOPE

For each cationic lipid, four aqueous suspensions were prepared, three containing the fusogenic neutral lipid DOPE (dioleoyl phosphatidyl ethanolamine), and one containing the cationic lipid only (Table II). For this, the solid cationic lipids were dissolved in chloroform and aliquots transferred to 5 ml glass tubes with Teflon-lined caps. DOPE, also dissolved in chloroform, was then added to individual tubes at 1:1, 2:1, or 3:1 molar ratios (ratio of cationic lipid to DOPE). The lipid mix was deposited as a film in the glass tube by evaporating the solvent with a stream of argon. The lipid film was hydrated with water (1 ml per mg total lipid) and then resuspended by sonication using a bath sonicator (three or four 15 s treatments with intermittent vortex mixing). The formulations were stored at 4 C. until used (usually within 8 weeks).

EXAMPLE 11

Cell Culture and Synthesis of Anionic Polymers

Cellular delivery and efficacy assays were carried out in monolayer cultures of cells originating from normal tissues or tumors (Table II, II and V). Cells were maintained in humidified incubators using growth medium recommended by the supplier. Hammerhead ribozymes were synthesized and purified using standard protocols (Wincott et al., 1995, 23, 2677; Beigelman et al., 1995, *J. Biol. Chem.* 270, 25702; both are incorporated by reference herein). Nuclease resistant linkages were incorporated at specific sites of the ribozymes, modifications that markedly increased the serum half-life from a few minutes to several hours. For cellular delivery studies, fluorophore-tagged 32-mer ribozymes were prepared by attaching a fluorescein or rhodamine moiety to the loop portion through a aminolinker-modified base (FIG. 13). An expression plasmid encoding the humanized Green Fluorescent Protein (plasmid pEGFP-C1) was obtained from Clontech.

EXAMPLE 12

Cellular Ribozyme Delivery

For the delivery studies, subconfluent cultures of mammalian cells were seeded in 24-well plates (~20,000 cells/ well) a day prior to the initiation of assay. In a typical delivery assay, 100 μl of a 1 μM fluorescein or rhodamine-conjugated ribozyme (i.e., 10×ribozyme diluted in water) was placed in a polystyrene tube, and an aliquot of the cationic lipid formulation was added at room temperature to allow complex formation. The appropriate growth medium added to each tube (0.9 ml) and then the contents were mixed and added to each well. Final concentration of the ribozyme was 100 nM and the transport vehicle concentration was varied from 2.5 to 20 μg/ml. After a 3–4 h incubation, the medium was replaced with normal growth medium and the localization of the cell-associated ribozyme was evaluated by fluorescence microscopy using a Nikon stage microscope equipped with a 40×objective and a ccd camera. In some studies, the total cell-associated ribozyme was quantified by FACS analysis.

EXAMPLE 13
Cellular Plasmid Delivery

Subconfluent cultures of cells were seeded in 24-well plates (~10,000 cells/well). In typical transfection studies, 100 ng of the plasmid in 0.1 ml water was premixed with individual lipids in a polyethylene tube and incubated at room temperature for ~10 minutes to allow complex formation. Then 0.9 ml growth medium (serum-free) was added to each tube, the contents were mixed, and administered to individual wells of cells for 3–4 h. The medium was then replaced with normal growth medium and cells were left for ~24 h. Expression of GFP was monitored by fluorescence microscopy. The transport vehicles that led to GFP expression in the highest percentage of cells were identified for each cell line (Table IV).

EXAMPLE 14
Cytotoxicity Analysis

The toxic effects of the lipid-formulated compositions on cells were determined in three ways. First, cellular morphology was evaluated in relation to normal, untreated cells and significant abnormalities or reduction in cell numbers were noted. Second, for evaluating gross toxicity, propidium iodide was added to the medium and the cells were examined for the presence of pink-red fluorescence in the nucleus, indicating the presence of perforated or damaged membranes. Finally, the longer term effect of the treatment on cells was quantified using a sensitive MTS proliferation assay (Promega).

EXAMPLE 15
c-myb Proliferation Assay

The protooncogene c-myb is a transcription factor that participates in regulating the proliferation of smooth muscle cells. It has been demonstrated that cells in which c-myb levels have been reduced by ribozyme-Lipofectamine treatment do not proliferate well in response to subsequent serum stimulation. Two ribozymes directed against c-myb termed "active" and "inactive" (Jarvis et al., 1995, RNA, 2, 419). Both ribozymes can recognize the mRNA target but only the "active" can cleave it. The "inactive" ribozyme serves as a negative control. In principle, the active ribozyme can reduce c-nvb expression by catalyzing the sequence-specific cleavage of the mRNA, leading to a reduction in cell proliferation. This assay was used to validate the utility of delivery formulations.3H-Thymidine Incorporation Assay In typical cell proliferation, subconfluent cultures of rat aortic smooth muscle cells (RASMC) were plated in 48-well plates in DMEM supplemented with amino acids, Hepes, and 10% fetal bovine serum (5000 cells/well/0.5 ml medium). Next day, cells were serum-starved, to inhibit proliferation, by replacing the medium with low serum medium (0.5% serum) for ~2 days. The starved cells were then treated with ribozyme-carrier formulations, usually 100 nM ribozyme premixed with 2.5–10 μg/ml carrier lipid, in serum-free medium for ~2 h, followed by "trafficking" in low serum-medium (0.25% serum) for ~20 h. Triplicate set of wells were exposed to each treatment. The cells were then stimulated to proliferate for 12 h in medium containing 10% serum. This was followed by another 8 h incubation in medium+10% serum+ $^3$H-thymidine (~1 μCi/ml). The cells were then fixed with ice-cold 10% trichloroacetic acid, washed twice with water, and $^3$H-thyrmidine incorporated into new DNA was measured by scintillation counting. The inhibition of proliferation using different ribozyme formulations is shown in Table V.

EXAMPLE 16
Cellular Transport of Lipophilic Compounds

Rhodamine-conjugated dioleoyl phosphatidyl ethanolamine (DOPE) was mixed with various cationic lipids and administered to cells seeded in 24-well plates. After ~3 h incubation, the cellular distribution of the fluorescent rhodamine-DOPE was examined by fluorescence microscopy. Every cell contained rhodamine (red fluorescence), indicating that the lipids were delivered efficiently to the cells. Next, fluorescein-conjugated ribozymes were packaged and coadministered to cells using the same vehicles using procedures described earlier. Again, every cell was labeled with rhodamine while a subset contained internalized ribozymes (green fluorescence). These observations suggested the lipid transporters can be used to deliver lipophilic as well as hydrophilic compounds to cells.

EXAMPLE 17
Delivery of Antisense Molecules

A 21-nucleotide long phosphorothioate oligodeoxynucleotide with an attached fluorescein moiety was synthesized by standard procedures. The oligonucleotide (100 nM) was formulated with different concentrations (2.5 to 10 μg/ml) of each transport vehicle and administered to cells. Subcellular distribution of the internalized material was evaluated by fluorescence microscopy. The results indicated that optimal transporter concentrations are different for antisense oligonucleotides compared to ribozymes.

EXAMPLE 18
Synthesis of $N^2,N^3$-di-oleyl-(N,N'-diguanidinoethyl-aminoethane)-2.3-diaminopropionic acid (36)

Referring to FIG. 14, applicant describes a reaction of 2,3-diaminopropionic acid 32 with oleoyl chloride in the presence of dimethylaminopyridine (DMAP) and triethylamine (TEA) can give the peracylated derivative 33, oleyl. Reaction of 33 with triethylenetetramine (TREN) 34, followed by reaction with 1H-Pyrazole-1-carboxamidine hydrochloride 35 can give the title compound 36.

EXAMPLE 19
Preparation of PC:CHOL:DOTAP:DSPE$_{2000}$ Liposome Formulation

Formation of EPC:CHOL:DOTAP:DSPE-PEG$_{2000}$: Egg yolk phosphatidylcholine (EPC), cholesterol, and DOTAP were purchased from Avanti Polar Lipids. DSPE-PEG$_{2000}$ (1,2-Distearoyl-sn-glycero-3-phosphoethanolamine-polythylene glycol-2000) was purchased from Shearwater polymers. Extruder was purchased from Lipex biomembranes. FPLC was purchased from Pharmacia. Radioactive compounds were purchased from NEN and ether from Sigma.

The following lipids suspended in chloroform were mixed together in a 50 ml round bottom flask: phosphatidylcholine (egg yolk) (85.5 mg), cholesterol (21.8 mg), DOTAP (23.7 mg), ceramide-PEG C20 (61.8 mg) resulting in a molar ratio of 50:25:15:10. A tracer of Cholesteryl hexadecyl ether (CHE) (26 µCi) was added to monitor lipid concentration. The lipids were dried down by rotary evaporation and then resuspended in ether (9 ml). Ribozyme (25 mg) suspended in 1×phosphate buffered saline (3 ml) was added to the ether/lipid mixture and mixed together into an emulsion. The ribozyme was quantitated using a $^{32}P$ internally labeled ribozyme tracer (160 µCi). Liposome vesicles were formed by removing the ether under vacuum. Residual ether was removed by bubbling argon gas through the lipid-ribozyme mixture for 10 minutes. Vesicles were then passed through polycarbonate filters with 200 nm and 100 nm pores consecutively 6–10 times using an Extruder (Lipex Biomembranes, Vancouver, B. C.). Liposomes were purified from unencapsulated material using an FPLC column packed with DEAE sepharose CL-6B. Ribozyme and lipid concentration was determined by reading an aliquot of purified liposomes on a scintillation counter for both tritium and 32P. The counts indicated that 5.75 mg of ribozyme was present within liposome vesicles (23% encapsulation).

EXAMPLE 20
Blood Clearance Study Using the EPC:CHOL:DOTAP:D-SPE$_{2000}$ Liposome Formulation Female C57B1/6J weighing 20–25 g were used in this study with 3 mmol of lipid (36 mg ribozyme) by tail vein injection. The time points observed were 15 minutes, 1 hour, 4 hour, and 24 hours with 3 mice per group. The animals were euthanized by $CO_2$ asphyxiation. Upon cessation of breathing, the chest cavity was opened and blood sampled (200–500 µL) from the heart. Sampled blood was added to a heparinized microfuge tube and centrifuged for 10 minutes to separate plasma and blood cells. Plasma samples were treated with proteinase K containing buffer(100 mM NaCl, 10 mM tris (pH 8), 25 mM EDTA, 10% SDS). A portion of the sample was to scintillant and counted. The remaining sample was resolved on a polyacrylamide gel and intact ribozyme bands were quantitated using a phosphorimager (molecular devices). The results are shown in FIG. 15. Formulation of ribozyme with EPC:CHOL:DSPE:PEG C18 greatly enhances the circulation time of intact ribozyme in plasma. Twenty-four hours after an intravenous bolus injection of 2 mg/kg ribozyme formulated with EPC:CHOL:DSPE:PEG$_{2000}$, over 6% of the dose remained in the plasma. Average concentrations dropped from an average of 6631 ng/ml at 15 minutes to 2305 ng/ml at 4 hours. Since plasma concentrations were relatively high 24 hours after an injection, it can be assumed that the elimination half-life is on the order of hours if not days. In comparison, an intravenous bolus injection of 30 mg/kg is no longer detectable after approximately 3 hours. The elimination half-life of unformulated ribozyme is approximately 30 minutes in the mouse.

EXAMPLE 21
Plasmid DNA Delivery into Cells in Culture

One day prior to transfection, target cells were plated to a final confluency of 50 to 60% on a 48 well plate. Cells types tested in serum free conditions are RT-4 (human bladder carcinoma), EJ (human bladder carcinoma), PC-3 prostate cancer cell line), and MCF-7 (breast cancer cell line). The following cell types were tested in the presence of 10% serum in the media: RT-4, PC-3 and MCF-7 cells. DNA (1 µg of pEGFP-C1 C-terminal protein fusion vector (Clontech)) was added to a polystyrene tube followed by the addition of 1 ml of desired media. Following agitation, the cationic lipid was added to the tube (1.25, 2.5, 5, or 10 µg lipid/µg DNA), incubated at room temperature for 15 minutes and then mixed by vortexing. Media from plated cells was aspirated and then washed with either serum free or normal growth media. 200 µL of the DNA/cationic lipid mixture was added to each well of a 48 well plate. The cells were incubated at 37° C. for 3 to 5 hours for serum-free uptake and 18 to 24 hours for uptake in the presence of serum. Fluorescent cells were then counted using fluorescence microscopy. The transfection rate was determined by comparing the number of fluorescence positive cells to the total number of cells in the microscope field.

Toxicity was determined by adding 5 µL of a 0.5 mg/ml stock solution of propidium iodine (PI) (Boehringer Mannheim) prior to examination by microscopy. Migration of the red dye into the nucleus of a cell indicated toxicity and loss of cell viability. The results of plasmid delivery in serum free media are shown in table VI. The results of plasmid delivery in the presence of serum is shown in table VII.

FACS (fluorescence activated cell sorting) analysis was performed on PC-3 cells using several formulations and the results are shown in table VIII. Transfection was achieved using the protocol described above with the cells being incubated with DNA for 4 hours in serum free conditions. Cells were trypsinized off the plate, collected in serum containing growth media, and spun down for 5 minutes at 800 RPM. The supernatant was removed and the cells were brought up in 500 µL of FAC buffer (4% FBS in Hank's balanced salt solution(HBSS)). 10 µL of 0.5 mg/ml of PI was added prior to FACS sorting. The results indicate that applicant's formulations improve delivery of macromolecules compared to other compounds which are commercially available.

EXAMPLE 22
Preparation of Cationic Lipids Conjugated to Polyethylene Glycol Via Amide Bond Cationic lipid (100 mg), methoxypolyoxyethylenecarboxylic acid (725 mg), and 1,3-dicyclohexylcarbodiimide (DCC)(30 mg) were dissolved in chloroform (30 mL) and the solution was allowed to react at 50° C. overnight. The reaction mixture was filtered and hexane was added to the filtrate for purification by precipitation. The product (N'-palmityl-N'-oleyl-α-amino,γ-PEGamino-glycinamide) was re-precipitated using the same procedure and then dried in vacuo to obtain a PEG-conjugated lipid. In addition to carboxy-terminated PEG, N-hydroxysuccinimdie activated ester of PEG can be utilized in the above conjugation procedures.

Conjugation may also be carried out by formation of a carbamate bond. The reaction would be initiated by reacting imidazolylcarbonate activated hydroxy-terminated methoxypolyethylene glycol with amino groups of cationic lipids described above. The methods described herein are not limiting. Those skilled in the art will recognize that PEG can be readily conjugated to cationic lipids using techniques known in the art and are within the scope of this invention.

Other embodiments are within the following claims.

Table I
Characteristics of Naturally Occurring Ribozymes
Group I Introns
Size: ~150 to >1000 nucleotides.
Requires a U in the target sequence immediately 5' of the cleavage site.
Binds 4–6 nucleotides at the 5'-side of the cleavage site.

Reaction mechanism: attack by the 3'-OH of guanosine to generate cleavage products with 3'-OH and 5'-guanosine.
Additional protein cofactors required in some cases to help folding and maintainance of the active structure.
Over 300 known members of this class. Found as an intervening sequence in *Tetrahymena thermophila* rRNA, fungal mitochondria, chloroplasts, phage T4, blue-green algae, and others.
Major structural features largely established through phylogenetic comparisons, mutagenesis, and biochemical studies [1].
Complete kinetic framework established for one ribozyme [2,3,4,5].
Studies of ribozyme folding and substrate docking underway [6,7,8].
Chemical modification investigation of important residues well established [9,10].
The small (4–6 nt) binding site may make this ribozyme too nonspecific for targeted RNA cleavage, however, the Tetrahymena group I intron has been used to repair a "defective" β-galactosidase message by the ligation of new β-galactosidase sequences onto the defective message [11].
RNAse P RNA (M1 RNA)
Size: ~290 to 400 nucleotides.
RNA portion of a ubiquitous ribonudeoprotein enzyme.
Cleaves tRNA precursors to form mature tRNA [12].
Reaction mechanism: possible attack by $M^{2+}$—OH to generate cleavage products with 3'-OH and 5'-phosphate.
RNAse P is found throughout the prokaryotes and eukaryotes. The RNA subunit has been sequenced from bacteria, yeast, rodents, and primates.
Recruitment of endogenous RNAse P for therapeutic applications is possible through hybridization of an External Guide Sequence (EGS) to the target RNA [13,14].
Important phosphate and 2' OH contacts recently identified [15,16].
Group II Introns
Size: >1000 nucleotides.
Trans cleavage of target RNAs recently demonstrated [17, 18].
Sequence requirements not fully determined.
Reaction mechanism: 2'-OH of an internal adenosine generates cleavage products with 3'-OH and a "lariat" RNA containing a 3'-5' and a 2'-5' branch point.
Only natural ribozyme with demonstrated participation in DNA cleavage [19,20] in addition to RNA cleavage and ligation.
Major structural features largely established through phylogenetic comparisons [21].
Important 2' OH contacts beginning to be identified [22]
Kinetic framework under development [23]
Neurospora VS RNA
Size: ~144 nucleotides.
Trans cleavage of hairpin target RNAs recently demonstrated [24].
Sequence requirements not fully determined.
Reaction mechanism: attack by 2'-OH 5' to the scissile bond to generate cleavage products with 2',3'-cyclic phosphate and 5'-OH ends.
Binding sites and structural requirements not fully determined.
Only 1 known member of this class. Found in Neurospora VS RNA.
Hammerhead Ribozyme
(see text for references)
Size: ~13 to 40 nucleotides.
Requires the target sequence UH immediately 5' of the cleavage site.
Binds a variable number nucleotides on both sides of the cleavage site.
Reaction mechanism: attack by 2'-OH 5' to the scissile bond to generate cleavage products with 2',3'-cyclic phosphate and 5'-OH ends.
14 known members of this class. Found in a number of plant pathogens (virusoids) that use RNA as the infectious agent.
Essential structural features largely defined, including 2 crystal structures [25,26]
Minimal ligation activity demonstrated (for engineering through in vitro selection) [27]
Complete kinetic framework established for two or more ribozymes [28].
Chemical modification investigation of important residues well established [29].
Hairpin Ribozyme
Size: ~50 nucleotides.
Requires the target sequence GUC immediately 3' of the cleavage site.
Binds 46 nucleotides at the 5'-side of the cleavage site and a variable number to the 3'-side of the cleavage site.
Reaction mechanism: attack by 2'-OH 5' to the scissile bond to generate cleavage products with 2',3'-cyclic phosphate and 5'-OH ends.
3 known members of this class. Found in three plant pathogen (satellite RNAs of the tobacco ringspot virus, arabis mosaic virus and chicory yellow mottle virus) which uses RNA as the infectious agent.
Essential structural features largely defined [30,31,32,33]
Ligation activity (in addition to cleavage activity) makes ribozyme amenable to engineering through in vitro selection [34]
Complete kinetic framework established for one ribozyme [35].
Chemical modification investigation of important residues begun [36,37].
Hepatitis Delta Virus (HDV) Ribozyme
Size: ~60 nucleotides.
Trans cleavage of target RNAs demonstrated [38].
Binding sites and structural requirements not fully determined, although no sequences 5' of cleavage site are required. Folded ribozyme contains a pseudoknot structure [39].
Reaction mechanism: attack by 2'-OH 5' to the scissile bond to generate cleavage products with 2',3'-cyclic phosphate and 5'-OH ends.
Only 2 known members of this class. Found in human HDV. Circular form of HDV is active and shows increased nuclease stability [40]

1. Michel, Francois; Westhof, Eric. Slippery substrates. Nat. Struct Biol. (1994), 1(1), 5–7.
1. Lisacek, Frederique; Diaz, Yolande; Michel, Francois. Automatic identification of group I intron cores in genomic DNA sequences. J. Mol. Biol. (1994), 235(4), 1206–17.
2. Herschlag, Daniel; Cech, Thomas R. Catalysis of RNA cleavage by the Tetrahymena thennophila ribozyme. 1. Kinetic description of the reaction of an RNA substrate complementary to the active site. Biochemistry (1990), 29(44), 10159–71.
3. Herschlag, Daniel; Cech, Thomas R.. Catalysis of RNA cleavage by the Tetrahymena thermnophila ribozyme. 2. Kinetic description of the reaction of an RNA substrate that forms a mismatch at the active site. Biochemistry (1990), 29(44), 10172–80.

4. Knitt, Deborah S.; Herschlag, Daniel. pH Dependencies of the Tetrahymena Ribozyme Reveal an Unconventional Origin of an Apparent pKa Biochemistry (1996), 35(5), 1560–70.
5. Bevilacqua, Philip C.; Sugimoto, Naoki; Turner, Douglas H. A mechanistic framework for the second step of splicing catalyzed by the Tetrahymena ribozyme. Biochemistry (1996), 35(2), 648–58.
6. Li, Yi; Bevilacqua, Philip C.; Mathews, David; Turner, Douglas H. Thermodynamic and activation parameters for binding of a pyrene-labeled substrate by the Tetrahymena ribozyme: docking is not diffusion-controlled and is driven by a favorable entropy change. Biochemistry (1995), 34(44), 14394–9.
7. Baneree, Aloke Raj; Turner, Douglas H. The time dependence of chemical modification reveals slow steps in the folding of a group I ribozyme. Biochemistry (1995), 34(19), 6504–12.
8. Zarrinkar, Patrick P.; Williamson, James R. The P9.1-P9.2 peripheral extension helps guide folding of the Tetrahymena ribozyme. Nucleic Acids Res. (1996), 24(5), 854–8.
9. Strobel, Scott A.; Cech, Thomas R. Minor groove recognition of the conserved G.cntdot.U pair at the Tetrahymena ribozyme reaction site. Science (Washington, D.C.) (1995), 267(5198), 675–9.
10. Strobel, Scott A.; Cech, Thomas R. Exocyclic Amine of the Conserved G.cntdot.U Pair at the Cleavage Site of the Tetrahymena Ribozyme Contributes to 5'-Splice Site Selection and Transition State Stabilization. Biochemistry (1996), 35(4), 1201–11.
11. Sullenger, Bruce A.; Cech, Thomas R. Ribozymemediated repair of defective mRNA by targeted trans-splicing. Nature (London) (1994), 371(6498), 619–22.
12. Robertson, H. D.; Altman, S.; Smith, J. D. J. Biol. Chem., 247, 5243–5251 (1972).
13. Forster, Anthony C.; Altman, Sidney. External guide sequences for an RNA enzyme. Science (Washington, D.C., 1883) (1990), 249(4970), 783–6.
14. Yuan, Y.; Hwang, E. S.; Altman, S. Targeted cleavage of mRNA by human RNase P. Proc. Natl. Acad. Sci. USA (1992) 89, 8006–10.
15. Harris, Michael E.; Pace, Norman R. Identification of phosphates involved in catalysis by the ribozyme RNase P RNA. RNA (1995), 1(2), 210–18.
16. Pan, Tao; Loria, Andrew; Zhong, Kun. Probing of tertiary interactions in RNA: 2'-hydroxyl-base contacts between the RNase P RNA and pre-tRNA. Proc. Natl. Acad. Sci. U. S. A. (1995), 92(26), 12510–14.
17. Pyle, Anna Marie; Green, Justin B. Building a Kinetic Framework for Group II Intron Ribozyme Activity: Quantitation of Interdomain Binding and Reaction Rate. Biochemistry (1994), 33(9), 2716–25.
18. Michels, William J. Jr.; Pyle, Anna Marie. Conversion of a Group II Intron into a New Multiple-Turnover Ribozyme that Selectively Cleaves Oligonucleotides: Elucidation of Reaction Mechanism and Structure/Function Relationships. Biochemistry (1995), 34(9), 2965–77.
19. Zimmerly, Steven; Guo, Huatao; Eskes, Robert; Yang, Jian; Perlman, Philip S.; Lambowitz, Alan M. A group II intron RNA is a catalytic component of a DNA endonuclease involved in intron mobility. Cell (Cambridge, Mass.) (1995), 83(4), 529–38.
20. Griffin, Edmund A., Jr.; Qin, Zhifeng; Michels, Williams J., Jr.; Pyle, Anna Marie. Group II intron ribozymes that cleave DNA and RNA linkages with similar efficiency, and lack contacts with substrate 2'-hydroxyl groups. Chem. Biol. (1995), 2(11), 761–70.
21. Michel, Francois; Ferat, Jean Luc. Structure and activities of group II introns. Annu. Rev. Biochem. (1995), 64, 435–61.
22. Abramovitz, Dana L.; Friedman, Richard A.; Pyle, Anna Marie. Catalytic role of 2'-hydroxyl groups within a group II intron active site. Science (Washington, D.C.) (1996), 271(5254), 1410–13.
23. Daniels, Danette L.; Michels, William J., Jr.; Pyle, Anna Marie. Two competing pathways for self-splicing by group II introns: a quantitative analysis of in vitro reaction rates and products. J. Mol. Biol. (1996), 256(1), 31–49.
24. Guo, Hans C. T.; Collins, Richard A. Efficient trans-cleavage of a stem-loop RNA substrate by a ribozyme derived from Neurospora VS RNA. EMBO J. (1995), 14(2), 368–76.
25. Scott, W. G., Finch, J. T., Aaron, K. The crystal structure of an all RNA hammerhead ribozyme:Aproposed mechanism for RNA catalytic cleavage. Cell, (1995), 81, 991–1002.
26. McKay, Structure and function of the hammerhead ribozyme: an unfinished story. RNA, (1996), 2, 395–403.
27. Long, D., Uhlenbeck, O., Hertel, K. Ligation with hammerhead ribozymes. U.S. Pat. No. 5,633,133.
28. Hertel, K. J., Herschlag, D., Uhlenbeck, O. A kinetic and thermodynamic framework for the hammerhead ribozyme reaction. Biochemistry, (1994) 33, 3374–3385.Beigelman, L., et al., Chemical modifications of hammerhead ribozymes. J. Biol. Chem., (1995) 270, 25702–25708.
29. Beigelman, L., et al., Chemical modifications of hammerhead ribozymes. J. Biol. Chem., (1995) 270, 25702–25708.
30. Hampel, Arnold; Tritz, Richard; Hicks, Margaret; Cruz, Phillip. 'Hairpin' catalytic RNA model: evidence for helixes and sequence requirement for substrate RNA. Nucleic Acids Res. (1990), 18(2), 299–304.
31. Chowrira, Bharat M.; Berzal-Herranz, Alfredo; Burke, John M. Novel guanosine requirement for catalysis by the hairpin ribozyme. Nature (London) (1991), 354(6351), 320–2.
32. Berzal-Herranz, Alfredo; Joseph, Simpson; Chowrira, Bharat M.; Butcher, Samuel E.; Burke, John M. Essential nucleotide sequences and secondary structure elements of the hairpin ribozyme. EBB J. (1993), 12(6), 2567–73.
33. Joseph, Simpson; Berzal-Herranz, Alfredo; Chowrira, Bharat M.; Butcher, Samuel E. Substrate selection rules for the hairpin ribozyme determined by in vitro selection, mutation, and analysis of mismatched substrates. Genes Dev. (1993), 7(1), 130–8.
34. Berzal-Herranz, Alfredo; Joseph, Simpson; Burke, John M. In vitro selection of active hairpin ribozymes by sequential RNA-catalyzed cleavage and ligation reactions. Genes Dev. (1992), 6(1), 129–34.
35. Hegg, Lisa A.; Fedor, Martha J. Kinetics and Thermodynamics of Intermolecular Catalysis by Hairpin Ribozymes. Biochemistry (1995), 34(48), 15813–28.
36. Grasby, Jane A.; Mersmann, Karin; Singh, Mohinder; Gait, Michael J. Purine Functional Groups in Essential Residues of the Hairpin Ribozyme Required for Catalytic Cleavage of RNA. Biochemistry (1995), 34(12), 4068–76.
37. Schmnidt, Sabine; Beigelman, Leonid; Karpeisky, Alexander; Usman, Nassim; Sorensen, Ulrik S.; Gait, Michael J. Base and sugar requirements for RNA cleavage of essential nucleoside residues in internal loop B of the hairpin ribozyme: implications for secondary structure. Nucleic Acids Res. (1996), 24(4), 573–81.

[38]. Perrotta, Anne T.; Been, Michael D. Cleavage of oligoribonucleotides by a ribozyme derived from the hepatitis delta. virus RNA sequence. Biochemnistry (1992), 31(1), 16–21.

[39]. Perrotta, Anne T.; Been, Michael D. A pseudoknot-like structure required for efficient self-cleavage of hepatitis delta virus RNA. Nature (London) (1991), 350(6317), 434–6.

[40]. Puttaraju, M.; Perrotta, Anne T.; Been, Michael D. A circular trans-acting hepatitis delta virus ribozyme. Nucleic Acids Res. (1993), 21(18), 4253–8.

TABLE II

Cationic Lipid Formulations and Cellular Uptake

| Compound Name | Cationic Lipid Name | Cationic lipid: DOPE (molar ratio) | Formulation Name | Dose (µg/ml) | Nuclear Localization 0 = none; 5 =0 all | Cytoplasmid Localization |
|---|---|---|---|---|---|---|
| DS46596a | Arg-chol-2 BOCs | 1:0 | nc99 | 5 | 1 | punct. |
| | | | | 10 | 1 | punct. |
| | | 1:1 | nc25 | 5 | 2–3 | punct. |
| | | | | 10 | 3–4 | punct. |
| | | 2:1 | nc26 | 5 | 2–3 | punct. |
| | | | | 10 | 3 | punct. |
| | | 3:1 | nc27 | 2–4 | punct. | |
| | | | | 10 | 2–4 | punct. |
| DS46596b | Arg-chol-3 BOCs | 1:0 | nc100 | 5 | 1 | some clumps |
| | | | | 10 | 1 | some clumps |
| | | 1:1 | nc4 | 5 | 4 | punct. |
| | | | | 10 | 3 | punct. |
| | | 2:1 | nc5 | 1 | punct. | |
| | | | | 10 | 1 | punct. |
| | | 3:1 | nc6 | 5 | 1 | punct. |
| | | | | 10 | 1 | punct. |
| PHF55933 | Chol-methyl- | 1:1 | nc13 | 5 | 0 | bright punct. |
| | | | | 10 | 0 | very bright |
| | | 2:1 | nc14 | 5 | 0–1 | bright punct. |
| | | | | 10 | 0 | bright punct. |
| | | 3:1 | nc15 | 5 | 0 | bright punct. |
| | | | | 10 | 0 | very bright |
| AK52450 | Dimyristoyl-pyridoxal | 1:0 | nc108 | 5 | 0 | few clumps |
| | | | | 10 | 0 | |
| | | 1:1 | nc16 | 5 | 0 | |
| | | | | 10 | 0 | |
| | | 2:1 | nc17 | 5 | 0 | |
| | | | | 10 | 0 | |
| | | 3:1 | nc18 | 5 | 0 | |
| | | | | 10 | 0 | |
| JA59311 | Palmitoyl oleoyl glycyldiamino butyric acid | 1:0 | nc101 | 5 | 0–1 | some punct. |
| | | | | 10 | 3 | punct. |
| | | 1:1 | nc19 | 5 | 2 | some punct. |
| | | | | 10 | 1 | bright punct. |
| | | 2:1 | nc20 | 5 | 1, faint | punct. |
| | | | | 10 | 3, var. bright. | punct. |
| | | 3:1 | nc21 | 5 | 3 | bright punct. |
| | | | | 10 | 3 | bright punct. |
| PH55938 | Lys-chol. | 1:0 | nc104 | 5 | 0–1, few brt. | no punct. |
| | | | | 10 | 0–1 | clumps. |
| | | 1:1 | nc22 | 5 | 0–1 | bright punct. |
| | | | | 10 | 0–1 | bright punct. |
| | | 2:1 | nc23 | 5 | 0 | bright punct. |
| | | | | 10 | 0 | bright punct. |
| | | 3:1 | nc24 | 5 | 0 | punct. |
| | | | | 10 | 0 | bright punct. |
| AK52465 | N-cholesteryl-pyridoxamine | 1:0 | nc109 | 5 | 0–1, very faint | |
| | | | | 10 | 1, very faint | some clumps |
| | | 1:1 | nc28 | 5 | 0 | |
| | | | | 10 | 0–1 | |
| | | 2:1 | nc29 | 5 | 0 | |
| | | | | 10 | 0 | |

TABLE II-continued

Cationic Lipid Formulations and Cellular Uptake

| Compound Name | Cationic Lipid Name | Cationic lipid: DOPE (molar ratio) | Formulation Name | Dose ($\mu$g/ml) | Nuclear Localization 0 = none; 5 = all | Cytoplasmid Localization |
|---|---|---|---|---|---|---|
| | | 3:1 | nc30 | 5 | 0 | |
| | | | | 10 | 0 | |
| AK52468 | Beta-alanine palm.oleoyl-amide | 1:0 | nc110 | 5 | 3, bright | punct. |
| | | | | 10 | 3–4, bright | punct. |
| | | 1:1 | nc31 | 5 | 0 | punct. |
| | | | | 10 | 0 | punct. |
| | | 2:1 | nc32 | 5 | 0–1 | punct. |
| | | | | 10 | 2–3 | punct |
| | | 3:1 | nc33 | 5 | 0–1 | punct. |
| | | | | 10 | 3–4 | punct. |
| AK52471 | dipalmitoyl-deoxy-aminoethyl-carboxamido-Uridine | 1:0 | nc111 | 5 | 0 | punct. |
| | | | | 10 | 0–1 | punct./clumps |
| | | 1:1 | cn34 | 5 | 0 | clumps |
| | | | | 10 | 0 | clumps |
| | | 2:1 | nc35 | 5 | 0 | clumps |
| | | | | 10 | 0 | clumps |
| | | 3:1 | nc36 | 5 | 0 | clumps |
| | | | | 10 | 0 | clumps |
| AK52474 | palmitoyl-oleoyl-carboxamido-ethyl-pyridoxmine | 1:0 | nc112 | 5 | 0 | |
| | | | | 10 | 0 | |
| | | 1.1 | nc37 | 5 | 0 | faint punct. |
| | | | | 10 | 0–1 | faint punct. |
| | | 2:1 | nc38 | 5 | 0 | faint |
| | | | | 10 | 0 | faint punct. |
| | | 3:1 | nc39 | 5 | 0 | |
| | | | | 10 | 0 | faint punct. |
| PH55939 | | 1:0 | nc105 | 5 | 0–1 | punct. |
| | | | | 10 | 0–1 | punct. |
| | | 1:1 | nc40 | 5 | 0 | punct. |
| | | | | 10 | 0 | punct. |
| | | 2:1 | nc41 | 5 | 0–1 | punct/vac. |
| | | | | 10 | 2–3 | punct. |
| | | 3:1 | nc42 | 5 | 0–1 | punct. |
| | | | | 10 | 0–1 | bright punct. |
| PH55941 | | 1:0 | nc106 | 5 | 0–1 | punct., clumps |
| | | | | 10 | 0–1 | brt. punct. clumps |
| | | 1.1 | nc43 | 5 | 0–1 | punct. |
| | | | | 10 | 2–3 | heavy punct. |
| | | 2:1 | nc44 | 5 | 0–1 | heavy punct. |
| | | | | 10 | 0–1 | heavy punct. |
| | | 3:1 | nc45 | 5 | 0–1 | punct., clumps |
| | | | | 10 | 0–1 | punct., clumps |
| PH55942 | | 1:0 | nc107 | 5 | 0–1 | bright punct. |
| | | | | 10 | 0–1 | bright punct. |
| | | 1:1 | nc46 | 5 | 0–1 | punct. |
| | | | | 10 | 3 | punct. |
| | | 2:1 | nc47 | 5 | 0–1 | punct. |
| | | | | 10 | 0–1 | bright punct. |
| | | 3:1 | nc48 | 5 | 0–1 | punct. |
| | | | | 10 | 0–1 | bright p |
| JA59312 | plamitoyl oleoyl glycylamino-guanyl diamino-butyric acid | 1:0 | nc102 | 5 | 1 | bright punct. |
| | | | | 10 | 4 | bright punct. |
| | | 1:1 | nc49 | 5 | 3 | punct. |
| | | | | 10 | 4 | bright punct. |

TABLE II-continued

Cationic Lipid Formulations and Cellular Uptake

| Compound Name | Cationic Lipid Name | Cationic lipid: DOPE (molar ratio) | Formulation Name | Dose (μg/ml) | Nuclear Localization 0 = none; 5 =0 all | Cytoplasmid Localization |
|---|---|---|---|---|---|---|
| | | 2:1 | nc50 | 5 | 3–4 | bright punct. |
| | | | | 10 | 4 | bright punct. |
| | | 3:1 | nc51 | 5 | 4-5 | bright punct. |
| | | | | 10 | 5 | bright punct. |
| JA59314 | | 1:0 | nc103 | 5 | 0–1 | punct. |
| | | | | 10 | 0–1 | heavy punct. |
| | | 1:1 | nc52 | 5 | 0 | punct. |
| | | | | 10 | 0 | punct. |
| | | 2:1 | nc53 | 5 | 0 | punct. |
| | | | | 10 | 0 | punct. |
| | | 3:1 | nc54 | 5 | 0 | faint punct. |
| | | | | 10 | 0 | faint punct. |
| AK52475 | dipalmitoyl-deoxy-guanidino-ethyl-carboxamido-uridine | 1:0 | nc96 | 5 | 0–1 | some clumps |
| | | | | 10 | 0–1 | clumps |
| | | 1:1 | nc84 | 5 | 0 | clumps/st. to gl. |
| | | | | 10 | 0 | clumps/st. to gl. |
| | | 2:1 | nc85 | 5 | 0 | clumps/st. to gl. |
| | | | | 10 | 0 | clumps/st. to gl. |
| | | 3:1 | nc86 | 5 | 0 | clumps/st. to gl |
| | | | | 10 | 0 | clumps/st. to gl |
| JA59316 | palmityl-oleoyl-diamino-butyric acid | 1:0 | nc97 | 5 | 0 | heavy punct. |
| | | | | 10 | 0 | heavy punct. |
| | | 1:1 | nc87 | 5 | 0 | lt. punct./sticky |
| | | | | 10 | 0 | lt. punct./sticky |
| | | 2:1 | nc88 | 5 | 0 | lt. punct./sticky |
| | | | | 10 | 0 | lt. punct./sticky |
| | | 3:1 | nc89 | 5 | 0 | sticky/out |
| | | | | 10 | 0 | sticky/out |
| JA59317 | palmity-oleoyl-guanidine | 1:0 | nc98 | 5 | 0–1 | faint punct. |
| | | | | 10 | 0–1 | punct. |
| | | 1:1 | nc90 | 1–2 | punct. | |
| | | | | 10 | 2–3 | punct. |
| | | 2:1 | nc91 | 5 | 1–2 | punct. |
| | | | | 10 | 1–2 | punct. |
| | | 3:1 | nc92 | 5 | 1 | punct. |
| | | | | 10 | 1 | punct. |

TABLE III

| Cells | Description | Optimal cationic lipids (>50% nuclear uptake) |
|---|---|---|
| HS27 | human foreskin fibroblasts | nc49, nc50 |
| HUVEC | human umbilical vein endothelial | nc51, nc26 |
| RAOSMC | rat aortic smooth muscle | nc102, nc49 |
| SK-N-SH | human neuroblastoma | nc21, nc25 |
| EJ | human bladder carcinoma | nc21, nc49 |
| RT-4 | human bladder carcinoma | nc49, nc21 |
| MCF-7 | human breast carcinoma | nc21 |
| FEM | human melanoma | nc21 |
| 1205 | human melanoma | nc49 |
| PC-3 | human prostate carcinoma | nc49, nc21 |
| LN-CAP | human prostate carcinoma | nc110, nc21 |

Table III: Lipid-mediated delivery of ribozymes to various cell lines. Cells were treated with 100 nM fluorescein-conjugated ribozymes formulated with a panel of cationic lipids (selected from nc21, nc25, nc26, nc49, nc51, nc102, nc110; see Methods). Subcellular distribution of the ribozyme was determined by fluorescence microscopy. Presence of fluorescence in the nucleus indicated that the ribozyme had been transported across the cell membrane (unconjugated fluorescein does not remain in the nucleus). Lipid formulations that led to high nuclear delivery with no significant toxicity are shown.

TABLE IV

| Cells | Description | Optimal cationic lipids (% of cells with GFP) |
|---|---|---|
| SK-N-SH | human neuroblastoma | nc49 (40%) |
|  |  | nc101 (25%) |
|  |  | nc110 (20%) |
|  |  | nc32 (15%) |
| RASMC | rat aortic smooth muscle | nc110 (~5%) |
| RT-4 | human bladder carcinoma | nc101 (60%) |
|  |  | nc19 (20%) |
|  |  | nc110 (20%) |
| HS27 | human foreskin fibroblasts | nc101 (~5%) |

Table IV: Lipid-mediated delivery of plasmids to various cell lines. Cells were treated with 0.1–1 µg/ml of a green fluorescent protein (GFP) expression plasmid formulated with 2.5–15 µg/ml of selected lipid formulations (Table II), as described (Methods). The expression of GFP was monitored by fluorescence microscopy ~20 hours after transfection. Formulations that resulted in GFP expression by ~5% or more of the cells are indicated.

TABLE V

| Lipid (formulation) | Nuclear Uptake? | % Inhibition |
|---|---|---|
| JA59312 (nc102) | Y > 50% | 40% |
| JA59312 (nc49) | Y > 40% | 38% |
| JA59317 (nc98) | Y > 10% | 23% |
| JA59311 (nc101) | Y > 5% | 21% |
| JA59311 (nc20) | Y > 10% | 0% |
| PH55942 (nc48) | N (punct.) | 18% |
| AK52468 (nc33) | N (punct.) | 16% |
| JA59316 (nc97) | N (punct.) | 0% |
| PHF55933 (nc13) | N | 0% |
| PZH55938 (nc22) | N | 0% |

Table V. Inhibition of cell proliferation by different ribozymne formulations and correlation with cellular and nuclear delivery. An anti-myb ribozyme and its inactive version (control) were formulated with various lipids (Table II) and administered to rat smooth muscle cells as described (Methods). The relative activity of the active vs. inactive ribozyme is shown (% inhibition of proliferation). In parallel experiments, cells were treated with identical formulations of a fluorescein-conjugated ribozyme and its subcellular localization was observed by fluorescence microscopy (Y, nuclear delivery (% of positive cells); N, no visible nuclear delivery; punct., punctate cytoplasmic fluorescence). In general, formulations that led to improved delivery of the ribozyme to the cell and the nucleus also led to increased efficacy.

TABLE VI

Delivery of Green Fluorescent Protein Containing Plasmid into Cells in Culture

| Cell type | Formulation name | Compounds | Transfection rate | Optimal lipid dose | Toxicity |
|---|---|---|---|---|---|
| PC-3 | nc 19 | JA 59311:DOPE at 1:1 | 40–64% | 2.5 µg/ml | <10% |
| PC-3 | nc 20 | JA 59311:DOPE at 2:1 | 40–50% | 2.5 µg/ml | <5% |
| PC-3 | nc 101B | JA 59311 | 70–75% | 5 µg/ml | <10% |
| PC-3 | nc 102 | JA 59312 | 30–45% | 2.5 µg/ml | 10% |
| PC-3 | nc 110D | AK 52468 | 60% | 2.5 µg/ml | 5% |
| PC-3 | nc 122 | JA 59317 & JA 59311-2:1 | 55–65% | 2.5 µg/ml | 5–13% |
| PC-3 | nc 123 | JA 59317 & JA 59311-3:1 | 30–50% | 2.5 µg/ml | 5% |
| PC-3 | nc 128 | JA 59317 & PH 55942-2:1 | 35–70% | 2.5 µg/ml | <3–15% |
| PC-3 | nc 144 | JA 59311 & JA 59312-2:1 | 40–60% | 2.5 µg/ml | <3–10% |
| PC-3 | nc 145 | JA 59311 & JA 59312-3:1 | 50–70% | 2.5 µg/ml | <3–20% |
| PC-3 | nc 146B | JA 59311 & AK 52468-1:1 | 40–69% | 2.5 µg/ml | <3–8% |
| PC-3 | nc 148B | JA 59311 & AK 52648-3:1 | 25–70% | 2.5 µg/ml | 3–20% |
| PC-3 | nc 156B | JA 59312 & JA 59311 at 3:1 | 40–65% | 1.5 µg/ml | <5% |
| PC-3 | nc 168 | AK 52468 & JA 59312 at 2:1 | 33–75% | 2.5 µg/ml | 5–10% |
| PC-3 | nc 169 | AK 52468 & JA 59312 at 3:1 | 50–79% | 2.5 µg/ml | 5–10% |
| RT-4 | nc 101B | JA 59311 | 30 to 68% | 5 µg/ml | <10% |
| RT-4 | nc 121 | JA 59311 & PH 55942-3:1 | 8–30% | 5 µg/ml | <5% |
| RT-4 | nc 122 | JA 59317 & JA 59311-2:1 | 20% | 2.5 µg/ml | <6% |
| Rt-4 | nc 144 | JA 59311 & JA 59312-2:1 | 50% | 10 µg/ml | <10% |
| RT-4 | nc 145 | JA 59311 & JA 59312-3:1 | 50% | 10 µg/ml | <10% |
| EJ cells | nc 19 | JA 59311:DOPE at 1:1 | 40% | 5 µg/ml | 10% |
| EJ cells | nc 20 | JA 59311:DOPE at 2:1 | 20% | 5 µg/ml | 5–10% |
| EJ cells | nc 101B | JA 59311 | 25–35% | 10 µg/ml | 5% |
| EJ cells | nc 110D | AK 52468 | 30% | 5 µg/ml | <5% |
| EJ cells | nc 122 | JA 59317 & JA 59311-2:1 | 35% | 5 µg/ml | 10% |
| EJ cells | nc 144 | JA 59311 & JA 59312-2:1 | 40% | 2.5 µg/ml | <3% |
| EJ cells | nc 145 | JA 59311 & JA 59312-3:1 | 35% | 5 µg/ml | 5% |
| MCF-7 | nc 110D | AK 52468 | 20–30% | 2.5 µg/ml | 4–20% |
| MCF-7 | nc 121 | JA 59311 & PH 55942-3:1 | 10–40% | 5 µg/ml | 8–10% |
| MCF-7 | nc 146B | JA 59311 & AK 52468 at 1:1 | 50% | 5 µg/ml | 15% |
| COS-7 | nc 21 | JA59311:DOPE (3:1) | 40% | 2.5 µg/ml | <5% |

TABLE VI-continued

Delivery of Green Fluorescent Protein Containing Plasmid into Cells in Culture

| Cell type | Formulation name | Compounds | Transfection rate | Optimal lipid dose | Toxicity |
|---|---|---|---|---|---|
| COS-7 | nc 101 | JA 59311 | 50% | 5 µg/ml | <5% |
| COS-7 | nc 110 | AK 52468 | 40% | 5 µg/ml | <5% |
| HeLa | nc 145 | JA 59311 & JA 59312 (3:1) | 40–50% | 2.5 µg/ml | <5% |

TABLE VII

Delivery of Green Fluorescent Protein Containing Plasmid into Cells in Culture in the Presence of 10% serum

| Cell type | Formulation name | Compounds | Transfection rate | Optimal lipid dose | Toxicity |
|---|---|---|---|---|---|
| RT-4 | nc 193 | JA 59311-1:Tween80 at 1:1 | 5–40% | 10 µg/ml | <1–40% |
| RT-4 | nc 194 | JA 59311-1:Tween 80 at 2:1 | 10–20% | 10 µg/ml | <1–10% |
| RT-4 | nc 195 | JA 59311-1:Tween80 at 3:1 | 10–40% | 10 µg/ml | 5–10% |
| RT-4 | nc 196 | JA 5931 1-1:Tween80 at 4:1 | 20% | 5 µg/ml | <3% |
| RT-4 | nc 220 | JA 59349:Tween80 at 6:1 | 15–40% | 10 µg/ml | 5–10% |
| PC-3 | nc 110D | AK 52468 | 40% | 5 µg/ml | 8% |
| PC-3 | nc 194 | JA 59311-1:Tween80 at 2:1 | 20–45% | 10 µg/ml | <1–10% |
| PC-3 | nc 195 | JA 59311-1:Tween80 at 3:1 | 60% | 10 µg/ml | 10% |
| PC-3 | nc 218 | JA 59311-1:Tween80 at 3:1 | 40–70% | 10 µg/ml | 5–40% |
| PC-3 | nc 219 | JA 59349:Tween80 at 4:1 | 60–75% | 10 µg/ml | 10–20% |
| MCF-7 | nc 110D | AK 52468 | 50% | 2.5 µg/ml | 20% |

TABLE VIII

FACS analysis of plasmid delivery into PC-3 cells of serveral cationic lipids after 4 hours in serum free media. GFP = Green Fluorescent Protein.

| Formulation | Lipid Dose | Plasmid DNA | % GFP positive |
|---|---|---|---|
| Lipofectamine* | 1.25 µg/ml | 1 µg/ml | 3 |
|  | 2.5 µg/ml | 1 µg/ml | 24 |
| PFX-6* | 1.25 µg/ml | 1 µg/ml | 4 |
|  | 2.5 µg/ml | 1 µg/ml | 15 |
| nc 146 | 1.25 µg/ml | 1 µg/ml | 40 |
|  | 2.5 µg/ml | 1 µg/ml | 65 |
| nc 148 | 1.25 µg/ml | 1 µg/ml | 41 |
|  | 2.5 µg/ml | 1 µg/ml | 56 |
| nc 156 | 1.25 µg/ml | 1 µg/ml | 45 |
|  | 2.5 µg/ml | 1 µg/ml | 71 |
| nc 169 | 1.25 µg/ml | 1 µg/ml | 53 |
|  | 2.5 µg/ml | 1 µg/ml | 72 |

*commercially available cationic lipids

What is claimed is:

1. A cationic lipid having the formula I:

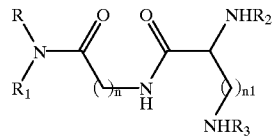

wherein, n is 1, 2 or 3 carbon atoms; $n_1$ is 2, 3, 4 or 5 carbon atoms; R and $R_1$ independently represent C12–C22 alkyl chain which are saturated or unsaturated, wherein the unsaturation is represented by 1–4 double bonds; and $R_2$ and $R_3$ are independently H, acyl, alkyl, carboxamidine, aryl, acyl, substituted carboxamidine, polyethylene glycol (PEG), or a combination thereof.

2. The cationic lipid of claim 1, wherein said cationic lipid is N'-palmityl-N'-oleyl-alpha, gamma-diaminobutyryl-glycinamide.

3. The cationic lipid of claim 1, wherein said cationic lipid is N'-palmityl-N'-oleyl-N-gamma-carboxamidine-alpha, gamma-diaminobutyryl glycinamide.

4. The cationic lipid of claim 1, wherein said cationic lipid ion-pairs to a negatively charged polymer selected from the group consisting of RNA, DNA and protein.

5. The cationic lipid of claim 4, wherein said RNA and said DNA comprise one or more modifications.

6. The cationic lipid of claim 4, wherein said RNA is an enzymatic RNA.

7. The cationic lipid of claim 4, wherein said DNA is an enzymatic DNA.

8. The cationic lipid aggregate of claim 7 further comprising a neutral lipid.

9. The cationic lipid aggregate of claim 8, wherein said neutral lipid is dioleoylphosphotidylethanolamine.

10. The cationic lipid aggregate of claim 7 further comprising a neutral lipid.

11. The cationic lipid aggregate of claim 10, wherein said neutral lipid is dioleoylphosphotidylethanolamine.

12. The cationic lipid of claim 1, wherein said cationic lipid is linked to polyethylene glycol (PEG).

13. The cationic lipid of claim 12, wherein said PEG is between about 2000–5000 daltons inclusive.

* * * * *